US011266550B2

(12) United States Patent
Takaishi

(10) Patent No.: US 11,266,550 B2
(45) Date of Patent: Mar. 8, 2022

(54) ABSORBENT ARTICLE AND METHOD FOR PRODUCING SAME

(71) Applicant: Daio Paper Corporation, Ehime (JP)

(72) Inventor: Mina Takaishi, Ehime (JP)

(73) Assignee: Daio Paper Corporation, Ehime (JP)

(*) Notice: Subject to any disclaimer, the term of this patent is extended or adjusted under 35 U.S.C. 154(b) by 868 days.

(21) Appl. No.: 16/078,362

(22) PCT Filed: Feb. 9, 2017

(86) PCT No.: PCT/JP2017/004740
§ 371 (c)(1),
(2) Date: Aug. 21, 2018

(87) PCT Pub. No.: WO2017/145776
PCT Pub. Date: Aug. 31, 2017

(65) Prior Publication Data
US 2021/0186778 A1    Jun. 24, 2021

(30) Foreign Application Priority Data

Feb. 23, 2016    (JP) .............................. JP2016-031991

(51) Int. Cl.
*A61F 13/15*    (2006.01)
*A61F 13/84*    (2006.01)
(Continued)

(52) U.S. Cl.
CPC ........ *A61F 13/84* (2013.01); *A61F 13/15699* (2013.01); *A61F 13/15731* (2013.01);
(Continued)

(58) Field of Classification Search
CPC ............... A61F 13/84; A61F 13/15699; A61F 13/15731; A61F 13/49014; A61F 13/4902;
(Continued)

(56) References Cited

U.S. PATENT DOCUMENTS 5,114,781 A * 5/1992 Morman .................. D04H 3/14
428/198
2002/0016122 A1    2/2002 Curro et al.
(Continued)

FOREIGN PATENT DOCUMENTS

CN        10412937     11/2014
JP        2004532758   10/2004
(Continued)

OTHER PUBLICATIONS

Extended European Search Report for EP 17756217, dated Jul. 16, 2019.

*Primary Examiner* — Jacqueline F Stephens
(74) *Attorney, Agent, or Firm* — Andrus Intellectual Property Law, LLP

(57) ABSTRACT

An absorbent article includes a novel design printing portion suitable for a stretchable region. An absorbent article has an elastic film stretchable structure, in which an elastic film is stacked between a first sheet layer and a second sheet layer. The first sheet layer and the second sheet layer are bonded together directly or through the elastic film by a large number of sheet bonded portions arranged at intervals. A region having the elastic film stretchable structure includes a stretchable region. The stretchable region is contracted in a stretchable direction by a contraction force of the elastic film is extensible in the stretchable direction. A design printing portion is provided in a portion located in the stretchable region in the elastic film.

12 Claims, 23 Drawing Sheets

(51) Int. Cl.
*A61F 13/49* (2006.01)
*A61F 13/496* (2006.01)
*B29D 99/00* (2010.01)

(52) U.S. Cl.
CPC .... *A61F 13/4902* (2013.01); *A61F 13/49014* (2013.01); *A61F 13/4963* (2013.01); *B29D 99/0064* (2013.01); *A61F 13/49011* (2013.01); *A61F 2013/15869* (2013.01); *A61F 2013/49022* (2013.01); *A61F 2013/49025* (2013.01); *A61F 2013/8497* (2013.01)

(58) Field of Classification Search
CPC ........ A61F 13/4963; A61F 2013/15869; A61F 2013/49022; A61F 2013/49025; A61F 2013/8497; B29D 99/0064
USPC ............ 604/385.24, 385.25, 385.26, 385.27, 604/385.3, 385.22
See application file for complete search history.

(56) References Cited

U.S. PATENT DOCUMENTS

| | | |
|---|---|---|
| 2006/0047259 A1 | 3/2006 | Erdman et al. |
| 2007/0032766 A1 | 2/2007 | Lui et al. |
| 2007/0133127 A1 | 6/2007 | Stamm et al. |
| 2012/0253306 A1 | 10/2012 | Otsubo et al. |
| 2012/0271265 A1 | 10/2012 | Langdon |
| 2012/0284904 A1 | 11/2012 | Otsubo et al. |
| 2013/0310795 A1 | 11/2013 | Glahn et al. |
| 2014/0041786 A1 | 2/2014 | Henke et al. |
| 2014/0326397 A1 | 11/2014 | Homoelle et al. |
| 2015/0056424 A1 | 2/2015 | Muslet |
| 2015/0147539 A1 | 5/2015 | Thomas et al. |

FOREIGN PATENT DOCUMENTS

| | | |
|---|---|---|
| JP | 2009501603 | 1/2009 |
| JP | 2009536845 | 10/2009 |
| JP | 2011136095 | 7/2011 |
| JP | 2011161041 | 8/2011 |
| JP | 5250372 | 7/2013 |
| JP | 2014511739 | 5/2014 |
| JP | 2014-218081 | 11/2014 |
| JP | 5695789 | 4/2015 |
| JP | 2015515920 | 6/2015 |
| JP | 2015529581 | 10/2015 |
| WO | 2007133127 | 11/2007 |
| WO | 2014084230 | 6/2014 |

* cited by examiner

Fig. 4 (a)
Fig. 4 (b)
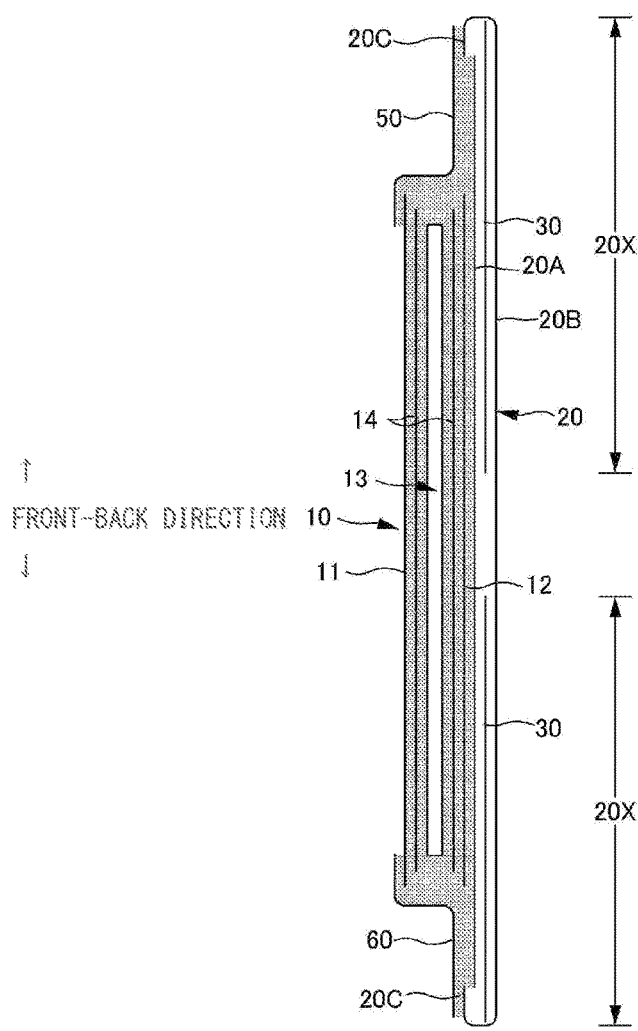
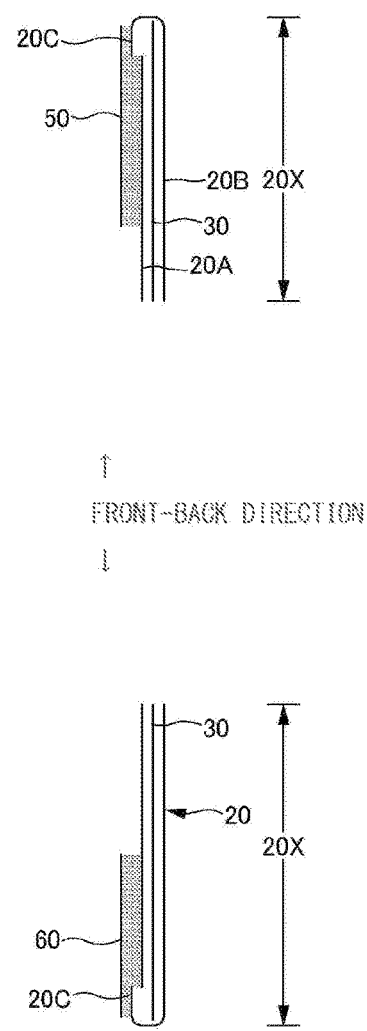

Fig. 9
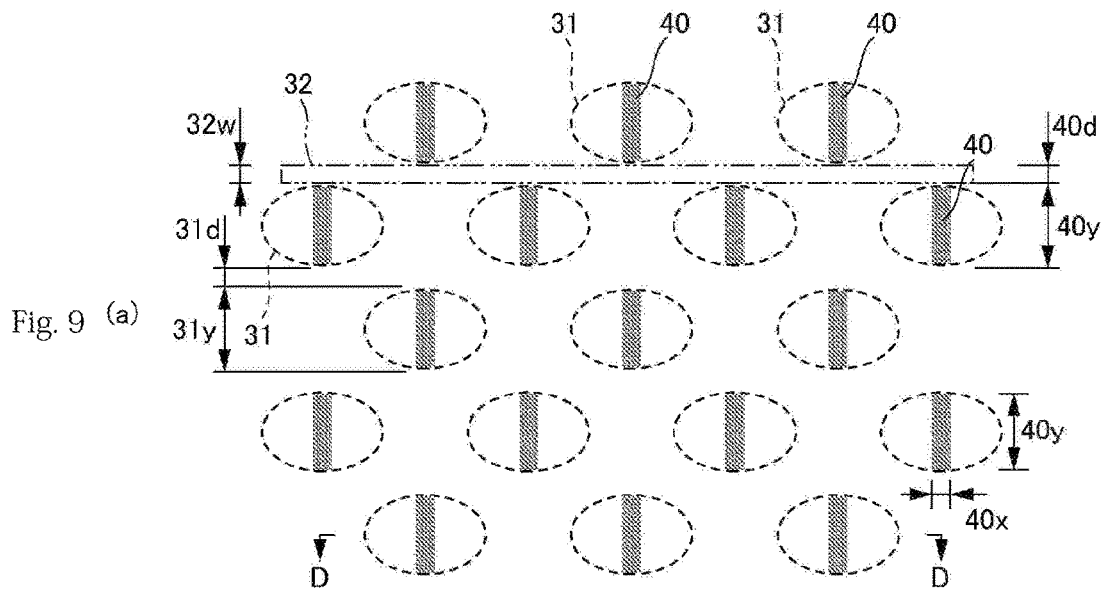
Fig. 9 (a)
←WIDTH DIRECTION (STRETCHING AND CONTRACTING DIRECTION)→
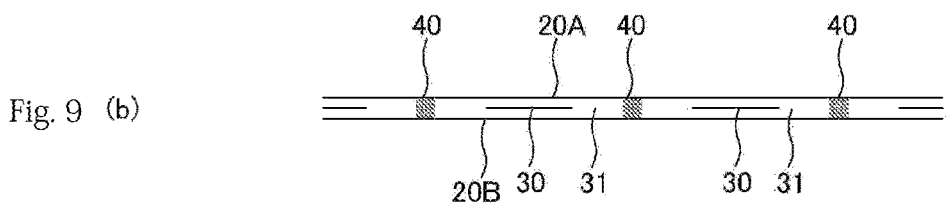
Fig. 9 (b)
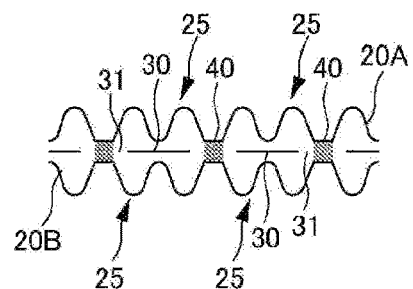
Fig. 9 (c)
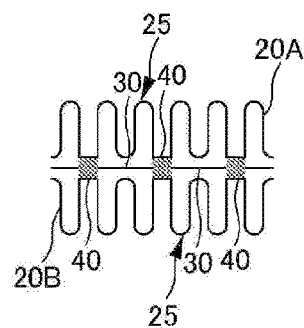
Fig. 9 (d)

← WIDTH DIRECTION (STRETCHING AND CONTRACTING DIRECTION) →

←WIDTH DIRECTION →
(STRETCHING AND
CONTRACTING DIRECTION)

←WIDTH DIRECTION →
(STRETCHING AND
CONTRACTING DIRECTION)

←WIDTH DIRECTION →
(STRETCHING AND
CONTRACTING DIRECTION)

←WIDTH DIRECTION →
(STRETCHING AND
CONTRACTING DIRECTION)

Fig. 16 (a)
Fig. 16 (b)
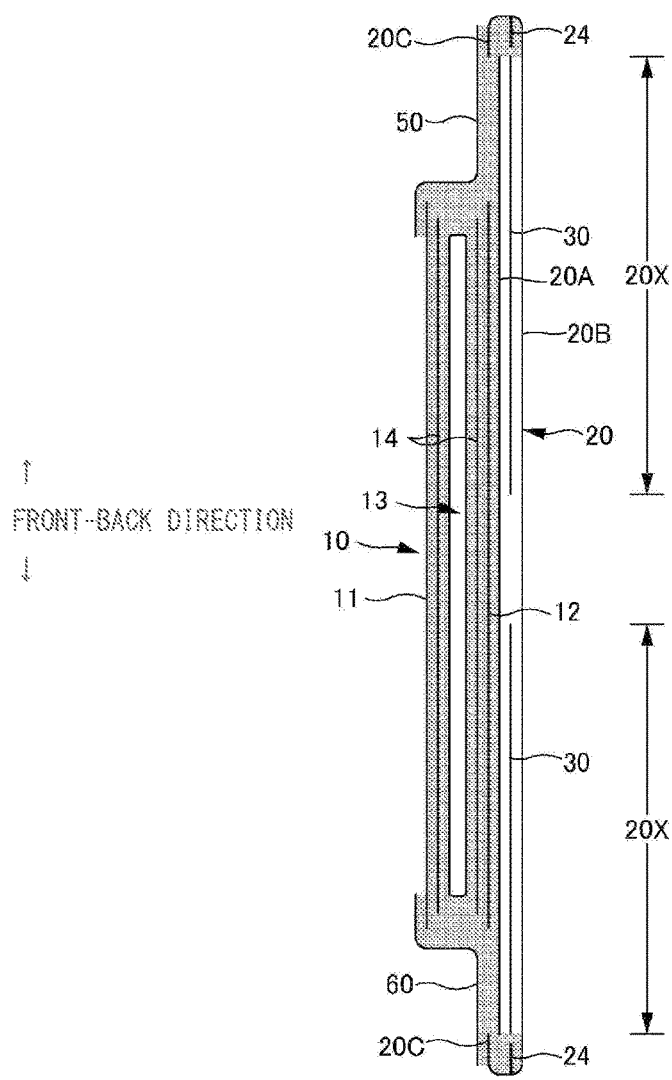
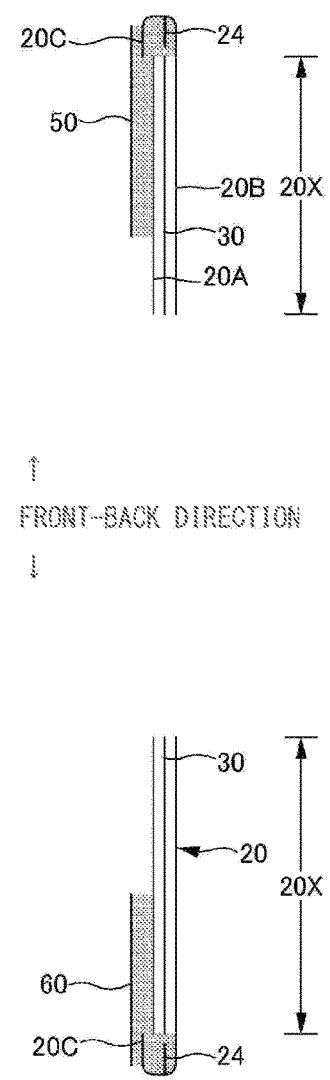

←STRETCHING AND CONTRACTING DIRECTION→

←STRETCHING AND CONTRACTING DIRECTION→

←STRETCHING AND CONTRACTING DIRECTION→

ABSORBENT ARTICLE AND METHOD FOR PRODUCING SAME

CROSS-REFERENCE TO RELATED APPLICATIONS

This application is the U.S. national stage application of International Application PCT/JP2017/004740, filed Feb. 9, 2017, which international application was published on Aug. 31, 2017, as International Publication WO 2017/145776 in the Japanese language. The International Application claims priority of Japanese Patent Application No. JP 2016-031991, filed Feb. 23, 2016. The international application and Japanese application are both incorporated herein by reference, in entirety.

TECHNICAL FIELD

The present invention relates to an absorbent article including a stretchable region having a design printing portion and a manufacturing method thereof.

BACKGROUND ART

Design such as a pattern for decoration (including an illustration and a one-point character), a function indication such as a usage method, usage guide, a size, etc., or a mark indication such as a manufacturer, a product name, a distinctive function, etc. is printed on the absorbent article (for example, see Patent Literatures 1 and 2).

In general, for a conventional design printing portion, the design is printed on a material such as a nonwoven fabric of an outer surface of an absorbent article, or a printed sheet is attached to the absorbent article.

However, these conventional schemes have a problem that design is seriously damaged due to stretching and contraction when the schemes are applied to the stretchable region, and thus the schemes are not suitable for the stretchable region. In addition, there is a problem that a high-quality appearance as a cloth product may not be obtained. For example, when printing is applied to the material of the stretchable region, wrinkles and pleats are formed on the material of the design printing portion in a natural length state, and an aesthetic appearance is impaired.

CITATION LIST

Patent Literature

Patent Literature 1: JP 2015-515920 A
Patent Literature 2: JP 5695789 B2
Patent Literature 3: JP 2004-532758 A
Patent Literature 4: JP 2009-536845 A
Patent Literature 5: JP 2011-136095 A
Patent Literature 6: JP 5250372 B2

SUMMARY OF INVENTION

Technical Problem

In this regard, a principal object of the invention is to provide an absorbent article having a novel design printing portion suitable for a stretchable region.

Solution to Problem

The invention solving the above-mentioned problem is described below.

<Invention Described in Claim 1>

An absorbent article having an elastic film stretchable structure in which an elastic film is stacked between a first sheet layer and a second sheet layer, and the first sheet layer and the second sheet layer are bonded together directly or through the elastic film by a large number of sheet bonded portions arranged at intervals, wherein a region having the elastic film stretchable structure includes a stretchable region, the stretchable region contracted in a stretchable direction by a contraction force of the elastic film is extensible in the stretchable direction, and a design printing portion is provided in a portion located in the stretchable region in the elastic film.

(Operational Advantage)

In the invention, the elastic film stretchable structure is adopted, and the design printing portion such as a pattern is provided in the portion located in the stretchable region in the elastic film. Although the elastic film is stretching and contracting, wrinkles and pleats are not formed, thus, the damage of design, which would be caused by formation of wrinkles and pleats on a design printing object, does not occur in the invention. In addition to the advantage of not affecting the elasticity of the stretchable region at all, the invention has advantages that the surface of the elastic film is excellent in printability when compared to the nonwoven fabric, and printing is less likely to peel off since a printed surface of the elastic film is covered with the first sheet layer and the second sheet layer.

<Invention Described in Claim 2>

The absorbent article according to claim 1, wherein at each of the sheet bonded portions, the first sheet layer and the second sheet layer are welded via a through-hole penetrating the elastic film and recesses are respectively formed in surfaces of the first sheet layer and the second sheet layer, the surfaces being not faced each other, either one of the first sheet layer and the second sheet layer is a shallower-uneven-layer having shallower recesses than those of the other layer, and the design printing portion is provided on a surface of the elastic film, the surface being on the shallower-uneven-layer side.

(Operational Advantage)

For example, when welding of the sheet bonded portions is performed by ultrasonic sealing, the recesses of unevenness, which are formed on the sheet layer on the anvil roll side, become deeper, whereas the recesses, which are formed on the opposite sheet layer, become shallower. This description is also applied to heat sealing. In the invention, the sheet layer having the shallower recesses is referred to as the shallower-uneven-layer. In the elastic film stretchable structure of the invention, the design printing portion on the elastic film is visually recognized through the first sheet layer or the second sheet layer. Therefore, when the design printing portion is provided on the elastic film on the shallower-uneven-layer side being shallower and uneven as described in this claim, there is an advantage that appearance of the design printing portion is improved.

<Invention Described in Claim 3>

The absorbent article according to claim 1 or 2, wherein the stretchable region is stretchable in only one direction, and the elastic film has a WIDTH-DECREASING rate of 25% or less in a direction orthogonal to the stretchable direction.

(Operational Advantage)

When the elastic film is stretched in one direction, a width in a direction orthogonal to a stretching direction is decreased toward a center in the stretchable direction depending on the amount of stretching, which is referred to as WIDTH-DECREASING (or Neck-in). When the elastic film is contracted from this state to the natural length, the width returns to the original width. In many cases, the amount of stretching in the stretchable direction changes depending on the position in the direction orthogonal to the stretchable direction so that the stretchable region in the absorbent article fits a body having complicated curved surfaces. In such a case, a degree of the WIDTH-DECREASING changes depending on the position in the direction orthogonal to the stretchable direction. Therefore, when the amount of stretching in the stretchable direction changes depending on the position in the direction orthogonal to the stretchable direction in providing the design printing portion on the elastic film in the portion located in the stretchable region as in the invention, the amount of deformation of the design printing portion due to the WIDTH-DECREASING of the elastic film changes depending on the position in the direction orthogonal to the stretchable direction, and there is concern that appearance may deteriorate. Therefore, when the design printing portion is provided on the elastic film in the portion located in the stretchable region as in the invention, it is desirable that the WIDTH-DECREASING rate is small, particularly 25% or less as described in this claim. Definition of the "WIDTH-DECREASING rate" will be described below.

<Invention Described in Claim 4>

The absorbent article according to any one of claims 1 to 3, wherein the elastic film stretchable structure includes a plurality of regions having different elongations at an elastic limit, and the design printing portion is not disposed at a boundary of the plurality of regions or at portions adjacent to the boundary on the both sides thereof in the elastic film.

(Operational Advantage)

When the design printing portion is provided on the elastic film, the design printing portion is deformed as the elastic film stretches and contracts. In this case, when the entire design printing portion uniformly stretches and contracts, a shape of the design printing portion is uniformly deformed, and thus an overall balance of the design printing portion can be maintained. However, the elastic film stretchable structure is provided with a plurality of regions having the different elongations at the elastic limit for obtaining an advantage that fitting, etc. may be changed depending on the sites. In a case in which a plurality of regions having the different elongations at the elastic limit is provided in this way, when the design printing portion straddling the boundary of the regions is included, there is concern that deformation may be nonuniform at both sides of the boundary, and appearance may deteriorate. Therefore, in the case in which the plurality of regions having the different elongations at the elastic limit is provided, it is a preferable mode that the design printing portion is not disposed at the boundary of the plurality of regions or at portions adjacent to the both sides thereof as described in this claim.

<Invention Described in Claim 5>

The absorbent article according to any one of claims 1 to 4, wherein the absorbent article is an underpants-type disposable diaper including an outer member disposed in a front body and a back body, an inner member fixed to the outer member, the inner member including an absorber, side seal portions at which both side portions of the outer member in the front body and both side portions of the outer member in the back body are bonded together, respectively, an annular lower torso portion, a waist opening, and a pair of left and right leg openings, and the outer member in at least one of the front body and the back body has the elastic film stretchable structure such that the stretchable direction of the stretchable region is a width direction, across a range corresponding to a space between the side seal portions totally in the width direction and at least partly in a front-back direction.

(Operational Advantage)

The underpants-type disposable diaper has a large stretchable region among absorbent articles, and has many usage modes as an alternative to underwear. Thus, in the underpants-type disposable diaper, the design printing portion such as a pattern is provided in the stretchable region in many cases, and appearance is important. Therefore, the invention is suitable for such a stretchable region of the underpants-type disposable diaper.

<Invention Described in Claim 6>

A method of manufacturing an absorbent article having an elastic film stretchable structure that includes a stretchable region stretchable in one direction, the method comprising:

in forming the elastic film stretchable structure, forming sheet bonded portions by bonding a first sheet layer and a second sheet layer directly or through an elastic film at a large number of positions arranged at intervals in a state in which the elastic film is interposed between the first sheet layer and the second sheet layer while being stretched in a stretchable direction of the stretchable region; and as the elastic film, using an elastic film on which a design printing portion is printed in advance in a portion to be the stretchable region, or printing the design printing portion in the portion to be the stretchable region in the elastic film in manufacturing line, prior to stretching of the elastic film.

(Operational Advantage)

It is possible to manufacture the absorbent article according to claim 1.

<Invention Described in Claim 7>

The method of manufacturing an absorbent article according to claim 6, further comprising:

in forming the elastic film stretchable structure, forming the sheet bonded portions by bonding directly the first layer sheet and the second layer sheet by ultrasonic sealing, which is performed with the first sheet layer, the elastic film, and the second sheet layer passed between an anvil roll and an ultrasonic horn in the state in which the elastic film is interposed between the first sheet layer and the second sheet layer while being stretched in the stretchable direction of the stretchable region; and supplying the elastic film such that the design printing portion is disposed in a surface of the elastic film, the surface being on a side opposite to the anvil roll side.

(Operational Advantage)

It is possible to manufacture the absorbent article according to claim 2. In particular, according to the manufacturing method, as for pleats formed on the first sheet layer and the second sheet layer of the stretchable region in the natural length state, the pleats of the sheet layer on the side being opposite to the anvil roll side are more neatly formed in order than those on the sheet layer on the anvil roll side, so that the appearance of the design printing portion is further improved also in this respect.

<Invention Described in Claim 8>

The method of manufacturing an absorbent article according to claim 6 or 7, wherein the elastic film has a WIDTH-DECREASING rate of 25% or less in a direction orthogonal to the stretchable direction.

(Operational Advantage)

It is possible to manufacture the absorbent article according to claim 3. In particular, when the elastic film having the low WIDTH-DECREASING rate as described in this claim is used, manufacturing stability is enhanced, and the invention is suitable for the printing in manufacturing line.

<Invention Described in Claim 9>

The method of manufacturing an absorbent article according to any one of claims 6 to 8, further comprising:

in forming the elastic film stretchable structure, forming a plurality of stretchable regions having different elongations at an elastic limit by making patterns of the sheet bonded portions different; and printing the design printing portion in portions to be the plurality of stretchable regions in the elastic film;

wherein in the printing, a region has the smaller elongation at the elastic limit, at the higher deformation rate, a deformed design contracted and deformed in the stretchable direction is printed.

(Operational Advantage)

When the design printing portion is provided on the elastic film, the design printing portion is deformed as the elastic film stretches and contracts. In this case, when the entire design printing portion uniformly stretches and contracts, a shape of the design printing portion is uniformly deformed, and thus an overall balance of the design printing portion can be maintained. However, the elastic film stretchable structure is provided with a plurality of stretchable regions having the different elongations at the elastic limit by making patterns of the sheet bonded portions different for obtaining an advantage that fitting, stretchable/non-stretchable and the like may be changed depending on the sites. Such plurality of regions having different elongations at the elastic limit is formed by a difference in extent of contracting of the elastic film after tension, which has been applied to the first sheet layer, the second sheet layer, and the elastic film therebetween, is released by cutting into individual products or parts, after the sheet bonded portions are formed in a manufacturing process. The extent of contracting (including a case of non-stretchable state in which contraction hardly occurs) of the elastic film is decreased to be lower than a stretch rate of the elastic film, which has been stretched before the sheet bonded portions are formed, and the degree of such decrease may be changed depending on the patterns of the sheet bonded portions. When the design printing portion is uniformly provided so as to be disposed in portions to be the plurality of regions in the elastic film, a deformation degree in the stretchable direction of the design printing portion differs for each region in the natural length state or the worn state, and the appearance deteriorates.

On the other hand, as described in this claim, the region has the smaller elongation at the elastic limit, that is, the region has the smaller extent of contracting after the sheet bonded portions are formed, at the higher deformation rate, a deformed design contracted and deformed in the stretchable design is printed. By doing so, a difference in deformation in the stretchable direction of the design printing portion depending on the regions can be reduced, and deterioration of appearance may be prevented. Here, the deformation rate means a percentage of a difference in length before and after contraction and deformation to a length before the contraction and deformation.

<Invention Described in Claim 10>

The method of manufacturing an absorbent article according to any one of claims 6 to 9, further comprising in forming the elastic film stretchable structure, a plurality of regions, which have different elongations at the elastic limit in a product state, is formed, wherein the design printing portion is not printed at a boundary of the plurality of regions or at portions adjacent to the boundary on the both sides thereof in the elastic film.

(Operational Advantage)

It is possible to manufacture the absorbent article according to claim 4.

Advantageous Effects of Invention

As described above, according to the invention, there is an advantage that an absorbent article has a novel design printing portion suitable for a stretchable region, etc.

BRIEF DESCRIPTION OF DRAWINGS

FIG. 4(a) is a C-C cross-sectional view of FIG. 1, and FIG. 4(b) is an E-E cross-sectional view of FIG. 1.

FIG. 9(a) is a plan view of the main part of the stretchable region, FIG. 9(b) is a D-D cross-sectional view of FIG. 9(a), FIG. 9(c) is a cross-sectional view in a worn state, and FIG. 9(d) is a cross-sectional view in a natural length state.

FIG. 16(a) is a C-C cross-sectional view of FIG. 15, and FIG. 16(b) is an E-E cross-sectional view of FIG. 15.

DESCRIPTION OF EMBODIMENTS

Figure 1:
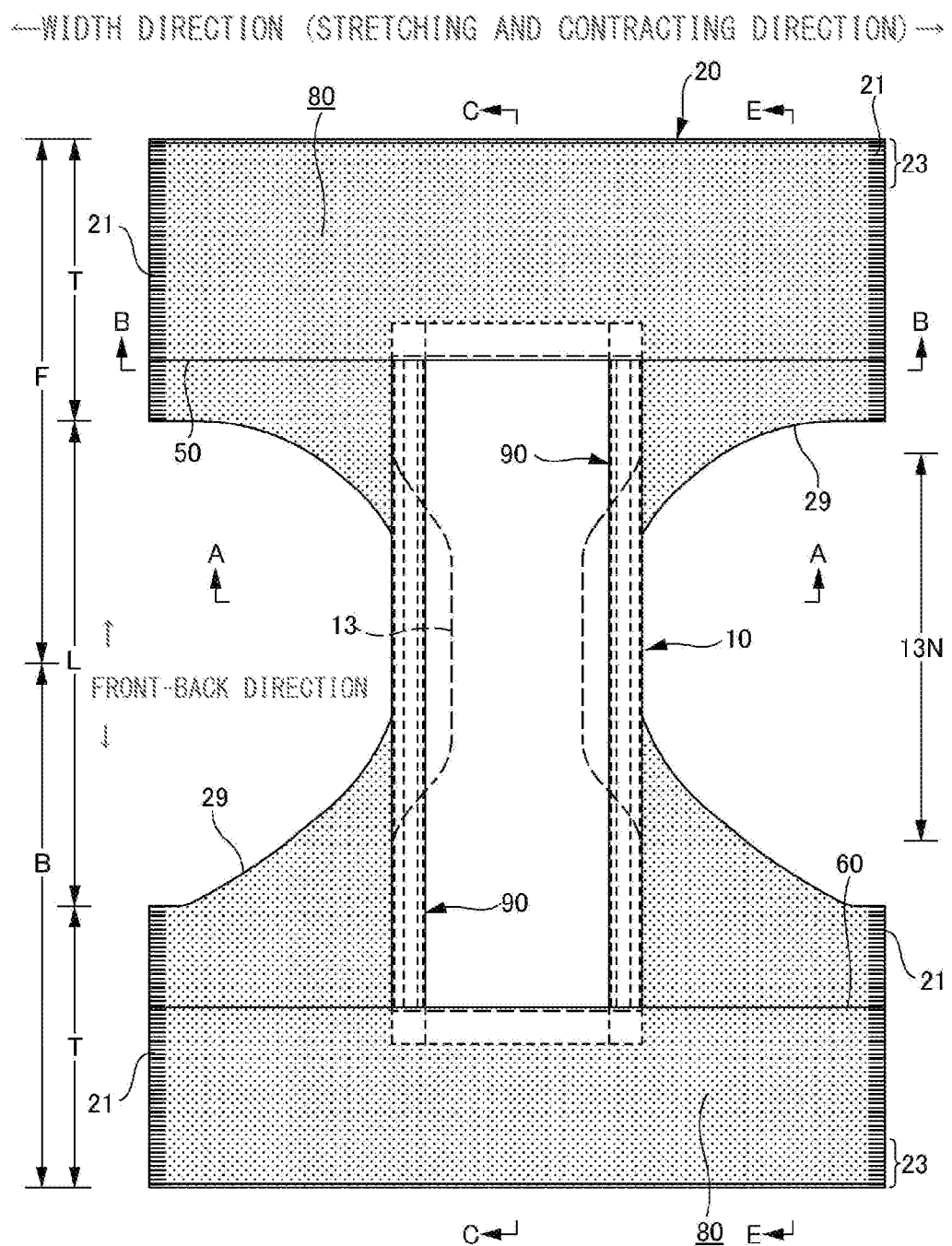
FIG. 1 is a plan view (internal surface side) of an underpants-type disposable diaper in a spread state.

Hereinafter, an embodiment of the invention will be described with reference to accompanying drawings. A dotted portion in a cross-sectional view indicates bonding means such as a hot-melt adhesive.

FIG. 1 to FIG. 6 illustrate an underpants-type disposable diaper. This underpants-type disposable diaper (hereinafter also simply referred to as a diaper) has an outer member 20 disposed in a front body F and a back body B and an inner member 10 that is fixed to the internal surface of the outer member as one unit. Further, in the inner member 10, an absorber 13 is interposed between a liquid pervious top sheet 11 and a liquid impervious sheet 12. In manufacturing, after a back surface of the inner member 10 is bonded to the internal surface (upper surface) of the outer member 20 using bonding means such as a hot-melt adhesive, the inner member 10 and the outer member 20 are folded at a center in a front-back direction (vertical direction) corresponding to a boundary between the front body F and the back body B, and both side portions thereof are bonded to each other by heat sealing, a hot-melt adhesive, etc. to form side seal portions 21, thereby obtaining an underpants-type disposable diaper in which a waist opening and a pair of right and left leg openings are formed.

(Exemplary Structure of Inner Member)

Figure 5:
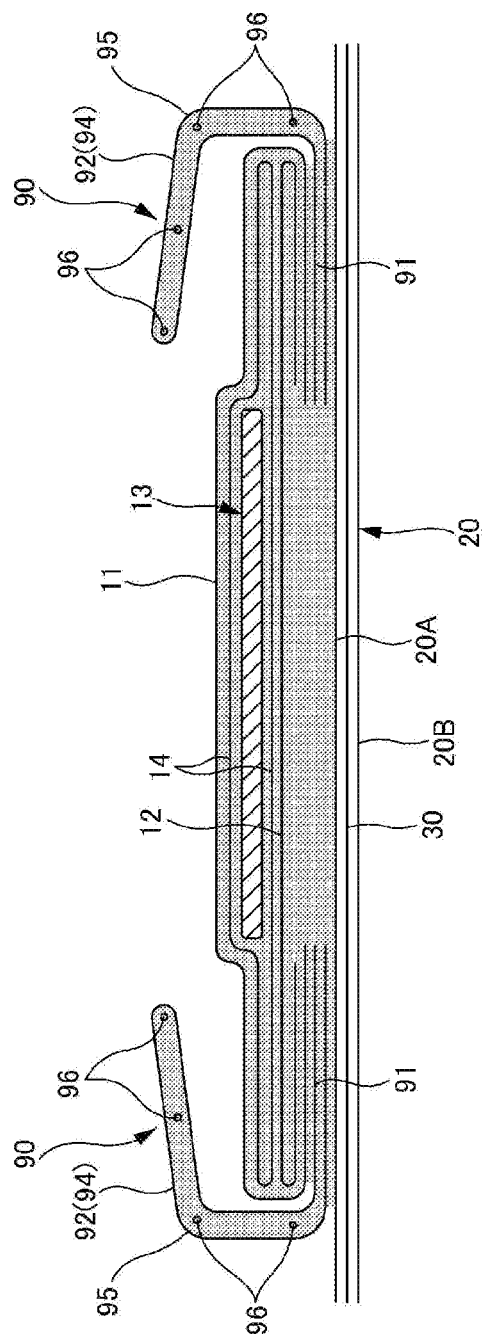
FIG. 5 is an A-A cross-sectional view of FIG. 1.
Figure 6:
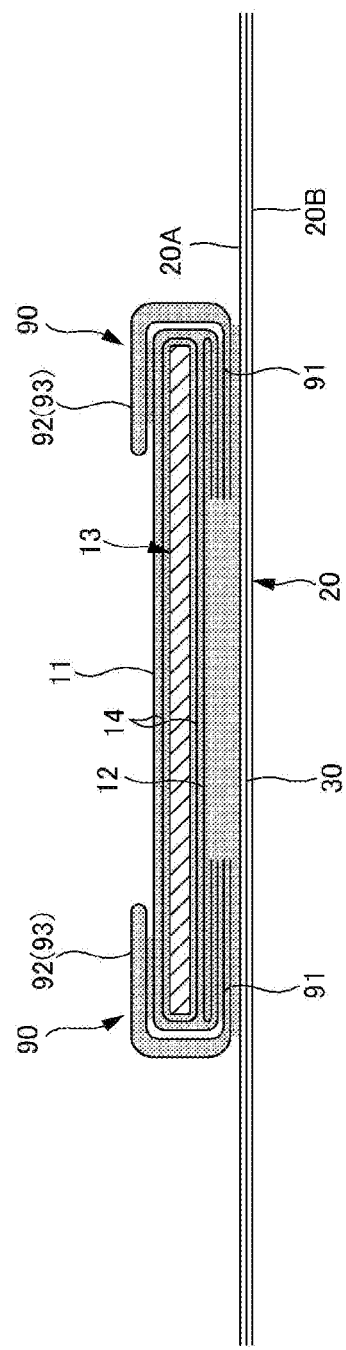
FIG. 6 is a B-B cross-sectional view of FIG. 1.

As illustrated in FIGS. 4 to 6, the inner member 10 has a structure in which the absorber 13 is interposed between the liquid pervious top sheet 11 and the liquid impervious sheet 12 made of polyethylene, etc., and absorbs and retains excretory fluid passing through the top sheet 11. The inner member 10 may have any planar shape and typically has a substantially rectangular shape as illustrated in FIG. 1.

The liquid pervious top sheet 11 that covers a front surface side (skin side) of the absorber 13 is preferably composed of perforated or imperforate nonwoven fabric or a porous plastic sheet. Examples of the raw fibers of the nonwoven fabric include synthetic fibers, such as olefin fibers, e.g., polyethylene and polypropylene, polyester fibers, and polyamide fibers; recycled fibers, such as rayon and cupra; and natural fibers, such as cotton. The nonwoven fabric can be produced by any process, for example, spun lacing, spun bonding, thermal bonding, melt blowing, or needle punching. Among these processes, preferred are spun lacing in view of flexibility and drape characteristics and thermal bonding in view of bulky soft products. A large number of through holes formed in the liquid pervious top sheet 11 facilitate absorption of urine and achieve dry touch characteristics. The liquid pervious top sheet 11 extends around the side edges of the absorber 13 and extends to the back surface side of the absorber 13.

For example, a liquid impervious plastic sheet such as polyethylene sheet or polypropylene sheet is used as the liquid impervious sheet 12 that covers the back surface side (non-skin contact side) of the absorber 13. Recently, permeable sheets have been preferably used in view of preventing stuffiness. This water-block permeable sheet is a micro-porous sheet prepared through melt-kneading an olefin resin, for example, polyethylene resin or polypropylene resin, and inorganic filler, forming a sheet with the kneaded materials, and then uniaxially or biaxially stretching the sheet.

The absorber 13 may be composed of a well-known basic component, such as an accumulated body of pulp fibers, an assembly of filaments, composed of, for example, cellulose acetate, or nonwoven fabric, and the absorber 13 may include as necessary high-absorbent polymer mixed or fixed to the basic component. The absorber 13 may be wrapped with a liquid-permeable and liquid-retainable wrapping sheet 14, such as a crepe sheet, to retain the shape and polymers, as required.

The absorber 13 has a substantially hourglass shape having at a crotch portion, a narrower part 13N with a width being narrower than those of the both front and back end portions of the absorber 13. The size of the narrower part 13N may be appropriately determined. The narrower part 13N may have a length of approximately 20 to 50% of the entire length of the diaper along the front-back direction, and the width, at the narrowest part, of approximately 40 to 60% of the entire width of the absorber 13. If the inner member 10 has a substantially rectangular planar shape in the case of the absorber with such a narrower part 13N, the inner member 10 has non-absorber side portions 17 free of the absorber 13 according to the narrower part 13N of the absorber 13.

Three-dimensional gathers 90, which are configured to fit around the legs, are formed on the both side portions of the inner member 10. As illustrated in FIG. 5 and FIG. 6, each of the three-dimensional gathers 90 includes a fixed portion 91 fixed to a side portion of the back surface of the inner member 10, a main body portion 92 extending from the fixed portion 91 around the side of the inner member 10 to the side portion of the front surface of the inner member 10, fallen portions 93 formed by fixing the front end portion and back end portion of the main body portion 92 to the side portion of the front surface of the inner member in a fallen state, and a free part 94 formed in an un-fixed state between the fallen portions 93. The three-dimensional gathers 90 are each composed of a gather sheet 95 obtained by folding a sheet such as a nonwoven fabric into a duplicate sheet. The gather sheet 95 is attached over the entire inner member 10 in the front-back direction, the fallen portion 93 is provided in front of and behind the non-absorber side portion 17, and the free part 94 extends to both front and back sides of the non-absorber side portion 17.

In addition, elongated gather elastic members 96 are disposed, for example, at a tip portion of the free part, between double gather sheets 95. As illustrated in FIG. 5, the free part 94 is erected by elastic contracting force of the gather elastic members 96 to form the three-dimensional gather 90 in a product state.

The liquid impervious sheet 12 is folded back to the back surface side together with the liquid pervious top sheet 11 at both sides of the absorber 13 in the width direction. It is desirable that the liquid impervious sheet 12 is opaque to block transmission of brown color of stool and urine. Preferred examples of the opacifying agent compounded in the plastic film include colorant or filler, such as calcium carbonate, titanium oxide, zinc oxide, white carbon, clay, talc, and barium sulfate.

The gather elastic member 96 may be composed of commodity materials, for example, styrene rubber, olefin rubber, urethane rubber, ester rubber, polyurethanes, polyethylene, polystyrene, styrene-butadiene, silicones, and polyester. The gather elastic members 96 preferably have a fineness of 925 dtex or less and are disposed under a tension of 150% to 350% at an interval of 7.0 mm or less to be hidden from outside view. The gather elastic member 96 may have a string shape illustrated in the drawing or a tape shape with an appropriate width.

Like the liquid pervious top sheet 11, the gather sheet 95 may be composed of raw fibers including synthetic fibers, such as olefin fibers of, for example, polyethylene fibers or polypropylene fibers; polyester fibers and amide fibers; recycled fibers of, for example, rayon and cupra; and natural fibers such as cotton. The gather nonwoven fabric may be prepared by any appropriate process, for example, spun bonding, thermal bonding, melt blowing, or needle punching. In particular, the basis weight should be reduced for production of a nonwoven fabric that can prevent stuffiness and has high air permeability. It is desirable that the gather sheet 95 is a water-repellent nonwoven fabric coated with a water repellent agent, for example, a silicone-based agent, a paraffin-metallic agent, or an alkyl chromic chloride agent to prevent permeability of urine, etc., to prevent diaper rash, and to enhance feeling to skin (dryness).

Figure 3:
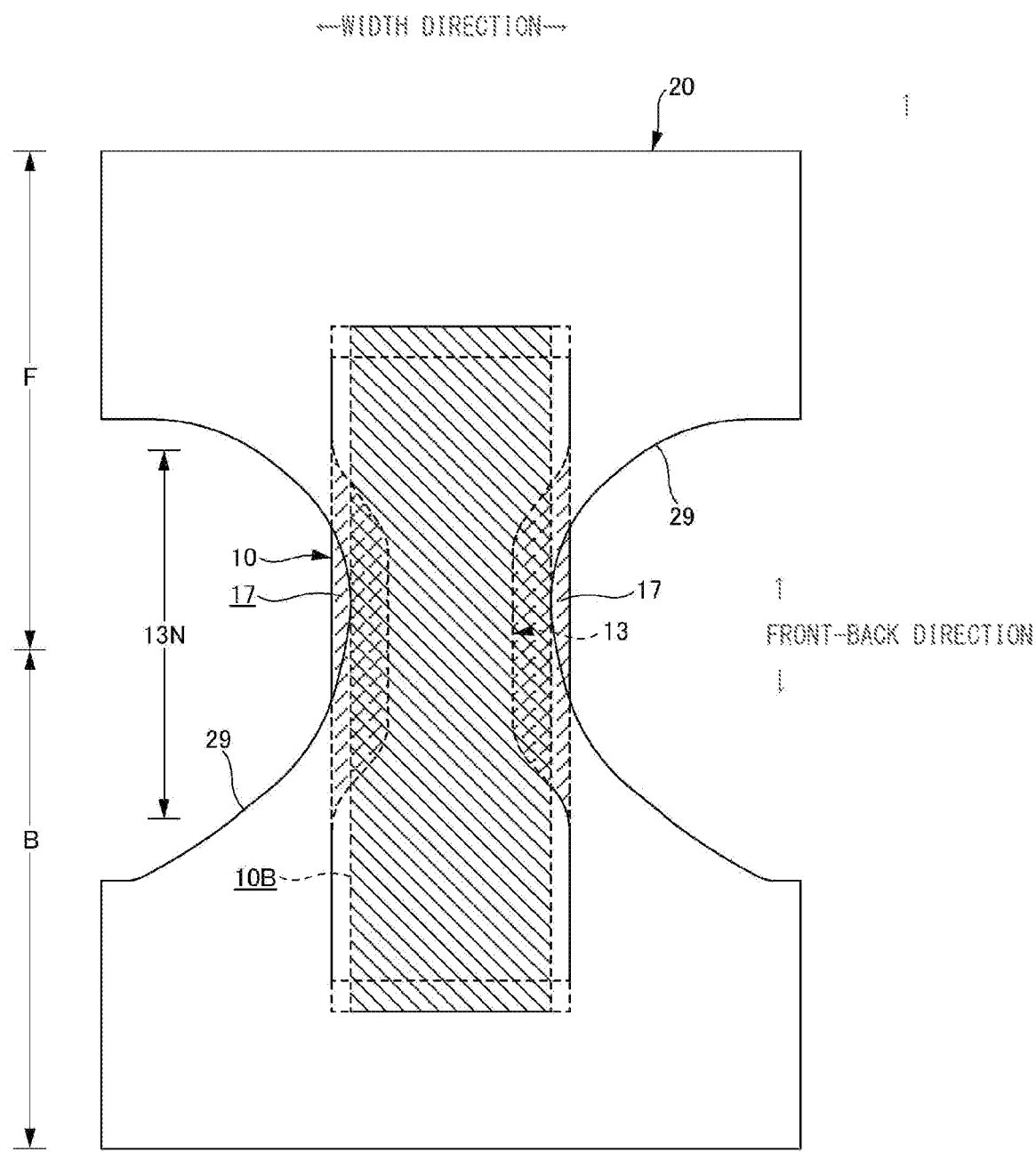
FIG. 3 is a plan view illustrating only a main part of the underpants-type disposable diaper in the spread state.

As illustrated in FIG. 3, the back surface of the inner member 10 is fixed to the internal surface of the outer member 20 by, for example, a hot-melt adhesive in an internal and external fixed region 10B (shaded area). The internal and external fixed region 10B extends across with a width from one non-absorber side portion 17 to the other non-absorber side portion 17 at the both front and back sides of the non-absorber side portions 17. Side edges of the internal and external fixed region 10B are preferably positioned at lateral sides of the middle of the non-absorber side portions 17 in the width direction. In particular, the internal and external fixed region 10B is preferably fixed to the substantially whole inner member 10 in the width direction and fixed to the substantially whole outer member 20 in the front-back direction.

(Front and Back Cover Sheets)

With reference to FIG. 1 and FIG. 4, front and back cover sheets 50 and 60 may be provided to cover the front and back end portions of the inner member 10 attached to the internal surface of the outer member 20 and to prevent leakage from the front and back edges of the inner member 10. The illustrated mode will be described in more detail. The front cover sheet 50 extends across the entire width of the front body F on the internal surface of the outer member 20 from an internal surface of the folded part 20C in a waist region 23 to a position overlapping with a front end portion of the inner member 10. The back cover sheet 60 extends across the entire width of the back body B on the internal surface of the outer member 20 from the internal surface of the folded part 20C in a waist region 23 to a position overlapping with the back end portion of the inner member 10. Minor non-bonded regions may be provided across the entire width (or only at a central portion) at edge portions of the front and back cover sheets 50 and 60 on the crotch side. The front and back cover sheets 50 and 60 having such non-bonded regions can prevent leakage of the adhesive and function as barriers against leakage when slightly suspended from the top sheet.

As in the illustrated mode, when the front and back cover sheets 50 and 60 are attached as separate components, there is an advantage that a range of choice of material is enlarged. However, there is a disadvantage that materials and manufacturing processes increase. Thus, the folded part 20C formed by folding back the outer member 20 toward the inner surface side of the diaper are respectively extended to portions overlapping with the inner member 10 to have the same function as that of the cover sheets 50 and 60.

(Structure Example of Outer Member)

Figure 7:
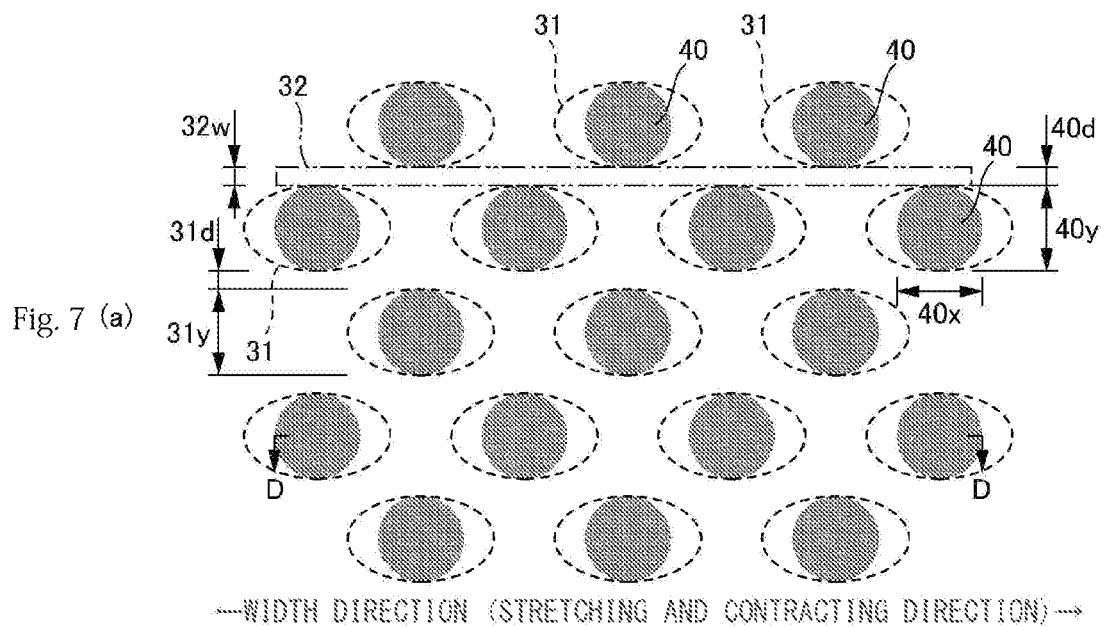
FIG. 7(a) is a plan view of a main part of a stretchable region.
FIG. 7(b) is a D-D cross-sectional view of FIG. 7(a)
FIG. 7(c) is a cross-sectional view in a worn state.
FIG. 7(d) is a cross-sectional view in a natural length state.
Figure 7:
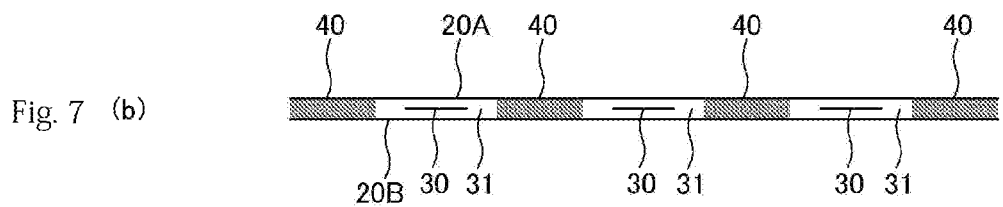
Figure 7:
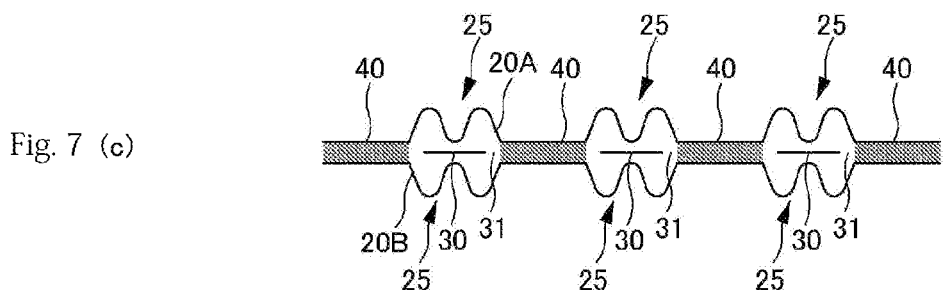
Figure 7:
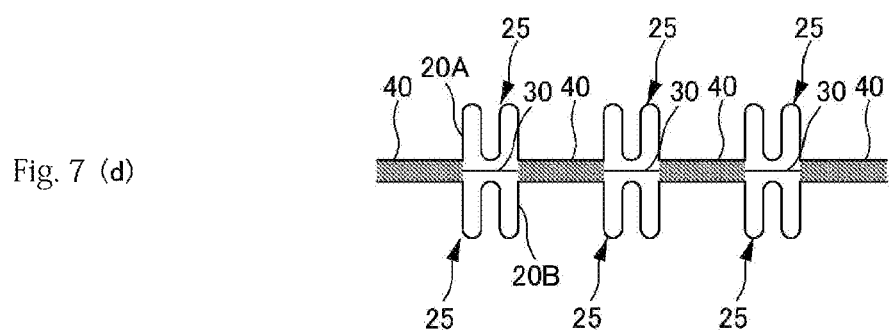

The outer member 20 extends from the side edge of the absorber 13 to a lateral side thereof. Referring to the outer member 20, in the crotch portion, a side edge of the outer member 20 may be positioned closer to a central side than a side edge of the inner member 10 in the width direction as in the illustrated mode, or may be positioned closer to an outer side than the side edge of the inner member 10 in the width direction. In addition, the outer member 20 has a lower torso portion T corresponding to a range in the front-back direction of each side seal portion 21, and an intermediate portion L corresponding to a range in the front-back direction between the lower torso portion T of the front body F and the lower torso portion T of the back body B. Further, in the outer member 20 of the illustrated mode, except for the middle of the intermediate region L in the front-back direction, an elastic film 30 is stacked between a first sheet layer 20A and a second sheet layer 20B, as illustrated in FIG. 2 and FIG. 4 to FIG. 6, and the first sheet layer 20A and the second sheet layer 20B have an elastic film stretchable structure 20X, a stretchable direction of which is corresponding to the width direction, bonded via through holes 31 penetrating the elastic film 30 at a large number of sheet bonded portions 40 arranged at intervals as illustrated in FIG. 7. The first sheet layer 20A and the second sheet layer 20B may be directly bonded through the elastic film 30 rather than via the through holes 31 of the elastic film 30. A planar shape of the outer member 20 is formed including concave-shaped leg lines 29 such that both side edges of the intermediate portion L in the width direction form the leg openings, and corresponds to a shape similar to an hourglass as a whole. The outer member 20 may be divided into the front body F and the back body B and disposed such that the front body F and the back body B are spaced apart from each other in the front-back direction in the crotch portion.

Figure 2:
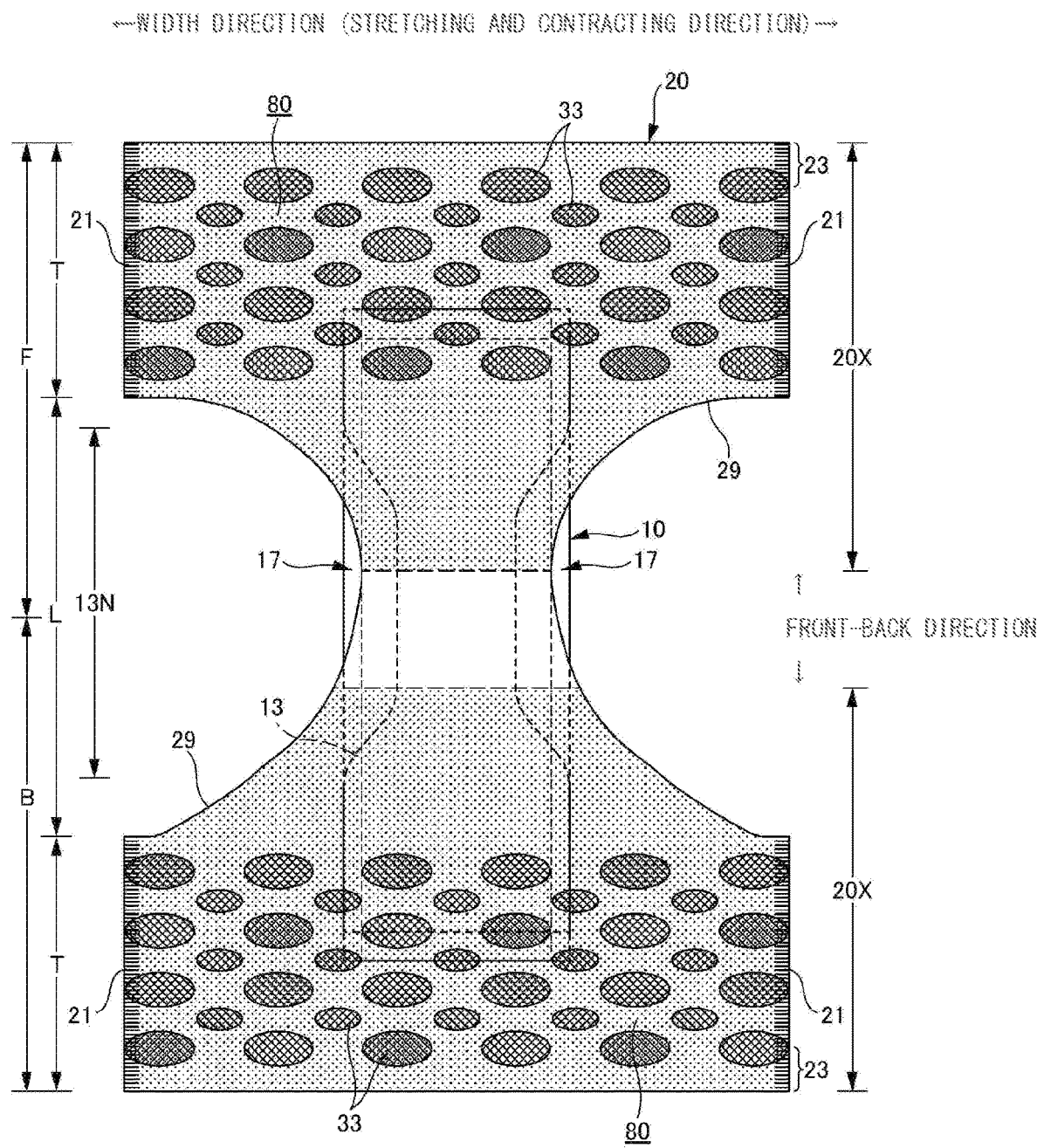
FIG. 2 is a plan view (external surface side) of the underpants-type disposable diaper in the spread state.
Figure 15:
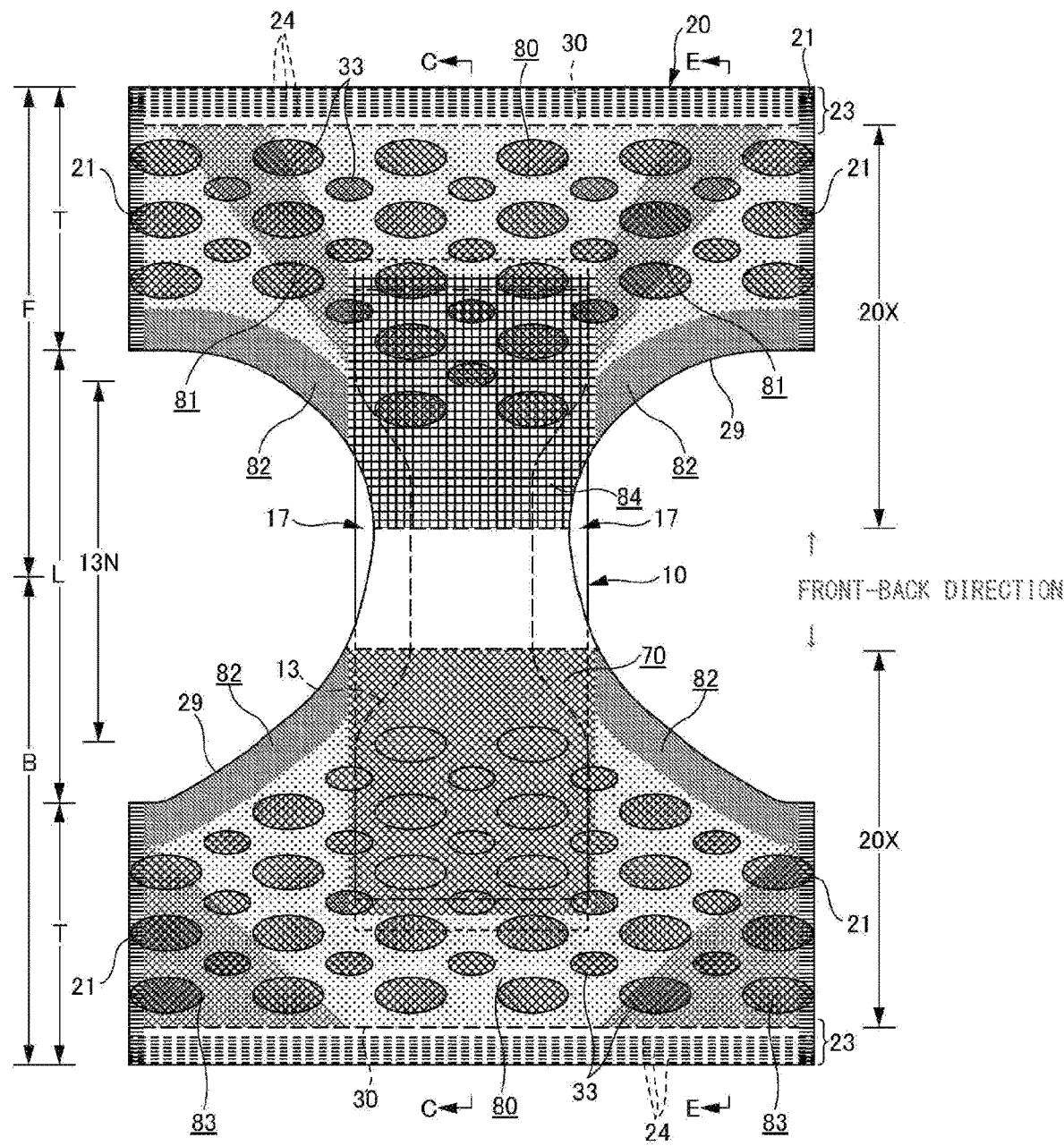
FIG. 15 is a plan view (external surface side) of the underpants-type disposable diaper in the spread state.

The modes illustrated in FIG. 1 and FIG. 2 correspond to a mode in which the elastic film stretchable structure 20X extends to the waist region 23. However, when the elastic film stretchable structure 20X is used in the waist region 23, tightening of the waist region 23 is insufficient. It is possible to provide a stretchable structure according to conventional elongated waist portion elastic members 24 as necessary without providing the elastic film stretchable structure 20X in the waist region 23 as illustrated in FIG. 15 and FIG. 16. However, elongated resilient and elastic members extending along the leg openings are not provided at the edge portions of the leg openings in the outer member 20. The waist portion elastic members 24 correspond to elongated elastic members such as a plurality of rubber threads disposed at intervals in the front-back direction, and apply a stretching force to tighten around the waist of the body. The waist portion elastic members 24 are not disposed substantially in a bundle with a close spacing, and three or more, preferably five or more members are disposed at intervals of about 3 to 8 mm to form a predetermined stretchable zone. A stretch rate of the waist portion elastic members 24 in fixing may be appropriately determined, and the stretch rate may be set to about 230 to 320% in the case of normal adult use. Rubber threads are used as the waist portion elastic members 24 in an illustrated example. However, for example, another elongated elastic member such as flat rubber may be used.

As another mode, although not illustrated, an appropriate modification may be made such that the elastic film stretchable structure 20X may not be provided in the intermediate portion L between the lower torso portion T of the front body F and the lower torso portion T of the back body B, the stretchable structure 20X may be continuously provided in the front-back direction from the inside of the lower torso portion T of the front body F to the inside of the lower torso portion T of the back body B through the intermediate portion L, or the elastic film stretchable structure 20X may be provided only in any one of the front body F and the back body B.

Figure 8:
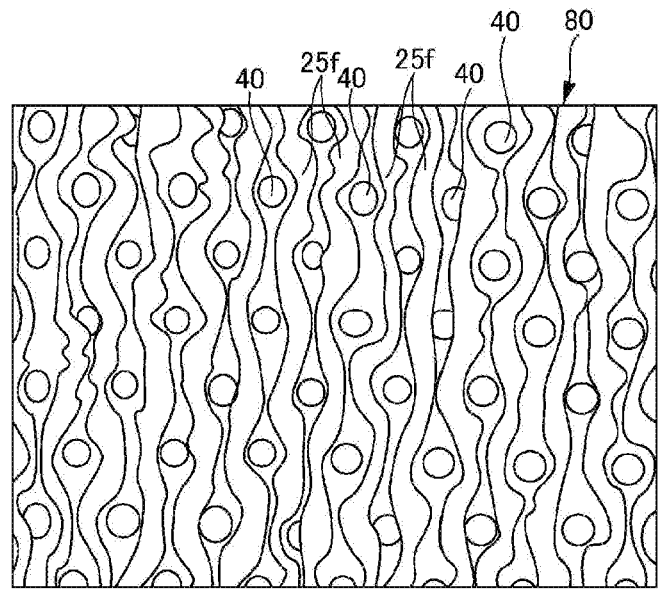
FIG. 8(a) is a trace diagram of a microscope photograph from a plane direction.
FIG. 8(b) is a trace diagram of a high-magnification microscope photograph from the plane direction.
FIG. 8(c) is a trace diagram of a high-magnification microscope photograph from an oblique direction in a stretchable region of a sample.
Figure 8:
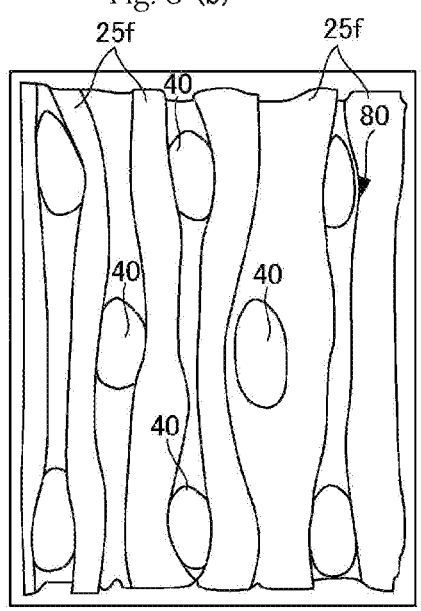
Figure 8:
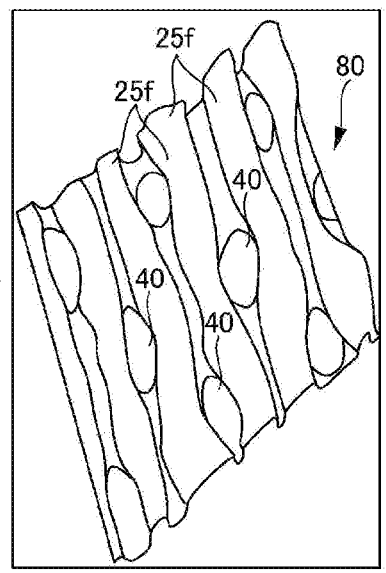
Figure 10A:
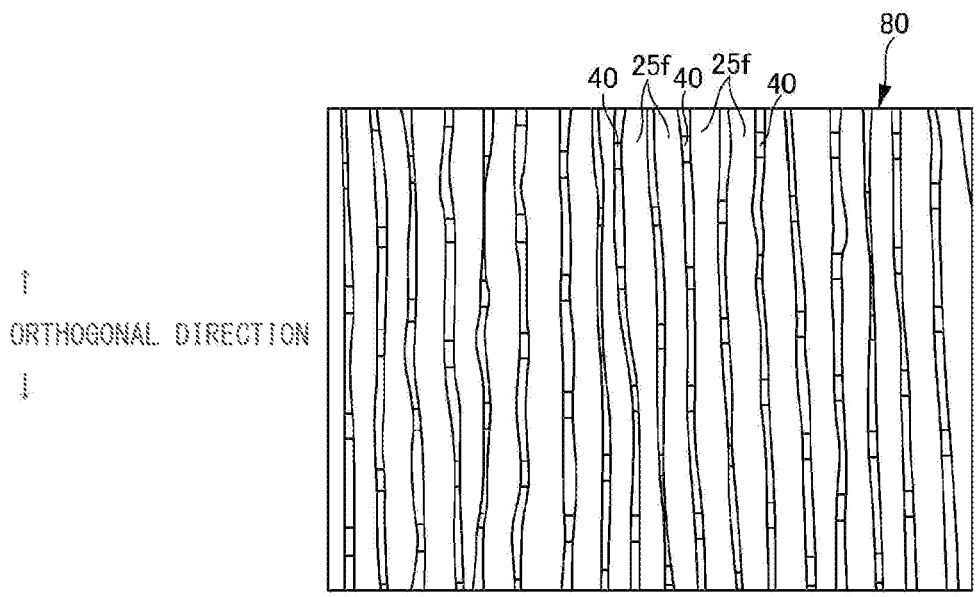
FIG. 10(a) is a trace diagram of a microscope photograph from the plane direction.
Figure 10:
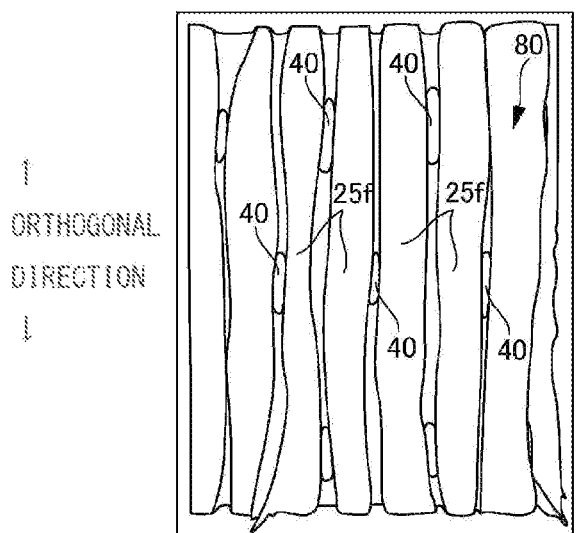
FIG. 10(b) is a trace diagram of a high-magnification microscope photograph from the plane direction.
FIG. 10(c) is a trace diagram of a high-magnification microscope photograph from the oblique direction in the stretchable region of the sample.
Figure 10:
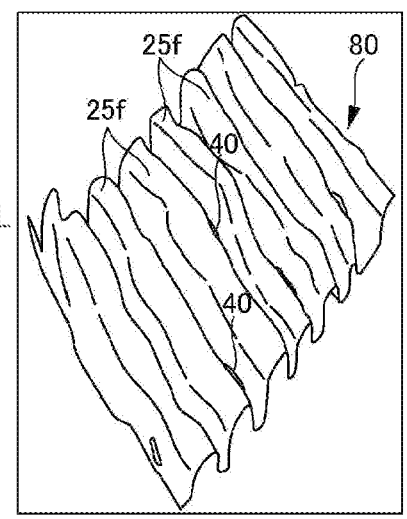
Figure 12:
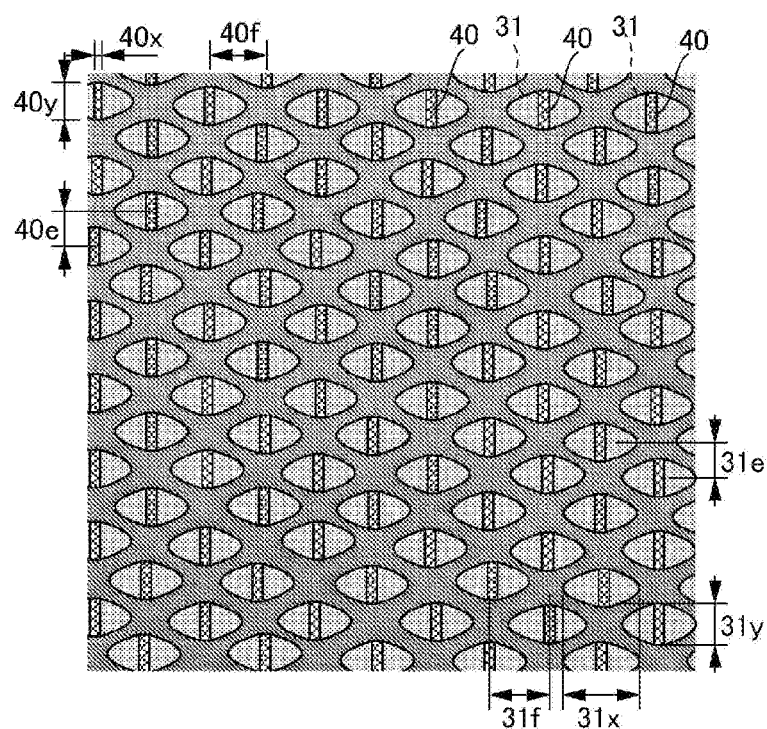
FIG. 12 is a trace diagram of a photograph of a non-stretchable region of a sample.
Figure 13:
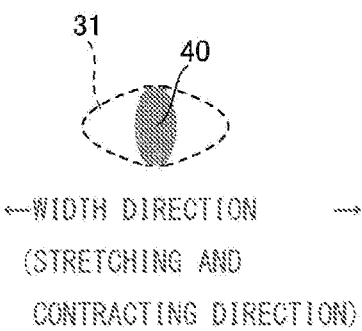
FIGS. 13(a)-13(d) are enlarged plan views of a main part of the non-stretchable region.
Figure 13:
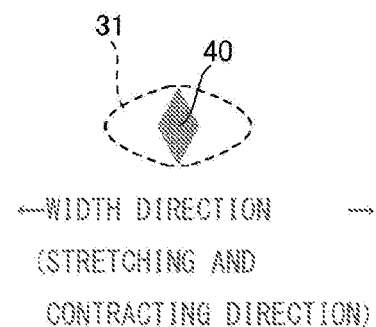
Figure 13:
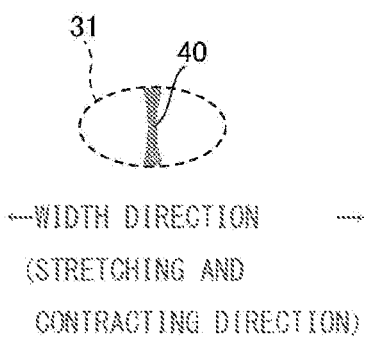
Figure 13:
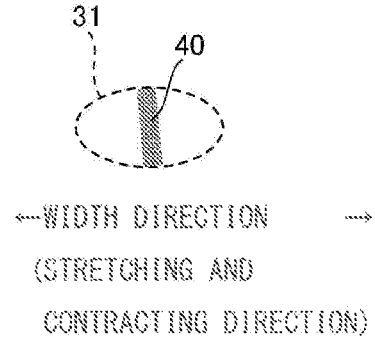

A shape of each of the sheet bonded portions 40 and a shape of each of the through holes 31 in a natural length state may be appropriately determined, and it is possible to adopt an arbitrary shape such as a perfect circle (see FIG. 7 and FIG. 8), an ellipse, a polygon such as a triangle, a rectangle (see FIG. 9 to FIG. 12), a rhombus (see FIG. 13(*b*)), etc., a convex lens shape (see FIG. 13(*a*)), a concave lens shape (see FIG. 13(*c*)), a star shape, a cloud shape, etc. The dimensions of each of the sheet bonded portions are not particularly restricted. However, a maximum length is preferably set to 0.5 to 3.0 mm, particularly 0.7 to 1.1 mm, and a maximum width 40*x* is preferably set to 0.1 to 3.0 mm, particularly 0.1 to 1.1 mm in a case of a shape which is long in a direction orthogonal to the stretchable direction.

A size of each of the sheet bonded portions 40 may be appropriately determined, and when the size is excessively large, the hardness of the sheet bonded portions 40 has a significant influence on touch. When the size is excessively small, a bonded area is small, and materials may not be sufficiently attached to each other. Thus, in general, an area of each of the sheet bonded portions 40 is preferably set to about 0.14 to 3.5 mm². An area of an opening of each of the through holes 31 may be greater than or equal to that of each of the sheet bonded portions since the sheet bonded portions are formed via the through holes 31, and the area is preferably set to about 1 to 1.5 times the area of each of the sheet bonded portions. The area of the opening of each of the through holes 31 refers to a value in a natural length state and in a state where the elastic film 30, the first sheet layer 20A and the second sheet layer 20B are provided in one unit, rather than a state of the elastic film 30 alone, and refers to a minimum value in a case in which the area of the opening of each of the through holes 31 is not uniform in a thickness direction such as a case in which the area is different between a front and a back of the elastic film 30.

Figure 21:
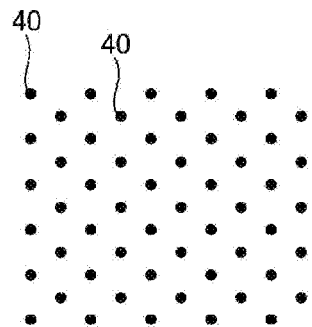
FIGS. 21(a)-21€ are plan views illustrating various arrangement examples of the sheet bonded portions.
Figure 21:
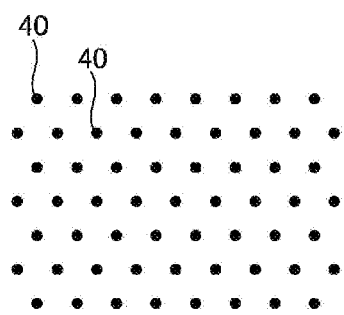
Figure 21C:
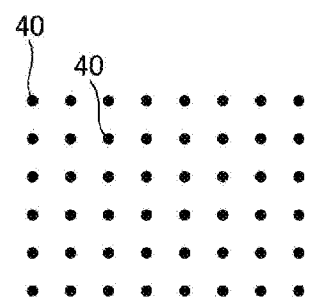
Figure 21:
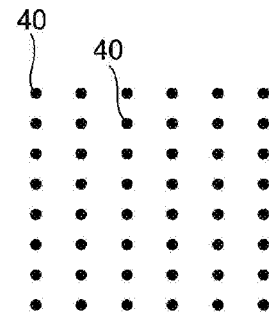
Figure 21:
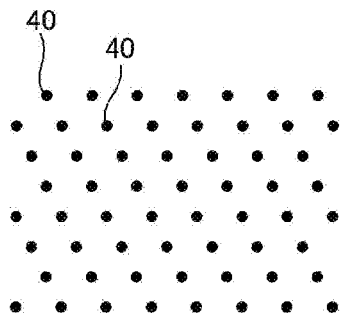

The planar geometries of the sheet bonded portions 40 and the through holes 31 may be appropriately determined. However, it is preferable to adopt a planar array in which the sheet bonded portions 40 and the through holes 31 are regularly repeated, such as an oblique lattice shape illustrated in FIG. 21(*a*), a hexagonal lattice shape (these shapes are also referred to as a staggered shape) illustrated in FIG. 21(*b*), a square lattice shape illustrated in FIG. 21(*c*), a rectangular lattice shape illustrated in FIG. 21(*d*), a parallelotope lattice shape illustrated in FIG. 21(*e*) (a mode in which two groups are provided such that a large number of parallel oblique row groups intersect each other illustrated in the drawings), etc. (including a mode in which these shapes are inclined at an angle less than 90 degrees with respect to the stretchable direction). Additionally, it is also possible to adopt a planar array in which a group of the sheet bonded portions 40 (arrangement of each group may be regular or irregular, and a pattern, a letter shape, etc. may be used) is regularly repeated.

When the first sheet layer 20A and the second sheet layer 20B are bonded in the sheet bonded portions 40 via the through holes 31 formed in the elastic film 30, it is desirable that neither the first sheet layer 20A nor the second sheet layer 20B is bonded to the elastic film 30 except at least between the first sheet layer 20A and the second sheet layer 20B in the sheet bond portions 40.

Bonding means for the first sheet layer 20A and the second sheet layer 20B in the sheet bonded portions 40 is not particularly restricted. For example, the first sheet layer 20A and the second sheet layer 20B in the sheet bonded portions 40 may be bonded using a hot-melt adhesive or bonding means based on material welding such as heat sealing, ultrasonic sealing, etc.

Figure 17:
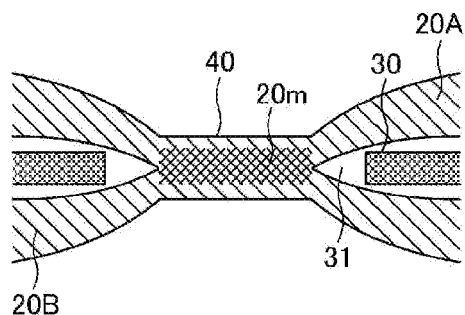
FIGS. 17(a)-17(c) are cross-sectional views schematically illustrating a cross section of a main part of an outer member stretched to a certain extent.
Figure 17:
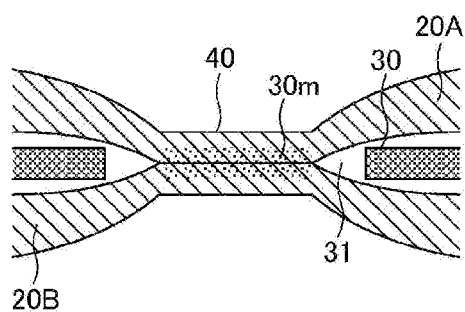
Figure 17:
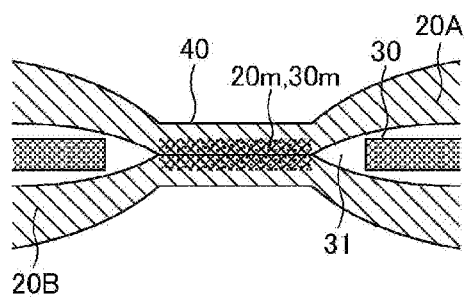
Figure 19:
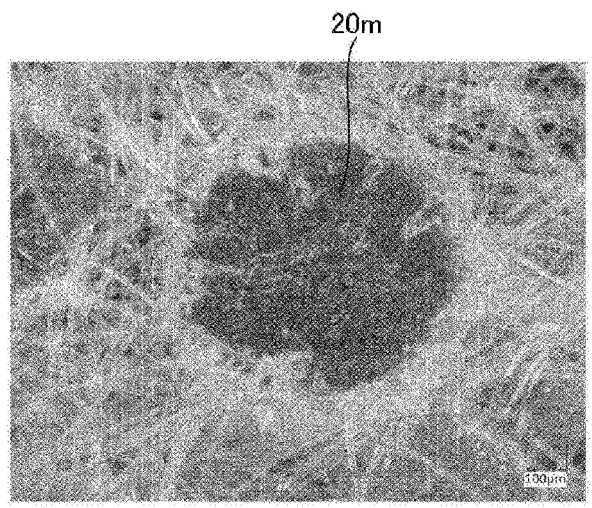
FIG. 19(a) is a plan photograph of a sheet bonded portion formed in a first welding mode.
FIG. 19(b) is a plan photograph of the sheet bonded portion formed in a third welding mode.
Figure 19:
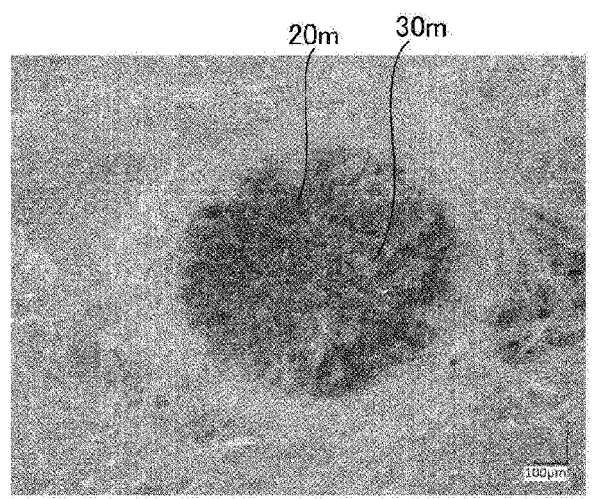

In the case in which the first sheet layer 20A and the second sheet layer 20B are bonded in the sheet bonded portions 40 via the through holes 31 of the elastic film 30, as a mode in which the sheet bonded portions 40 are formed by material welding, it is possible to adopt any one of a first welding mode (see FIG. 17(*a*)) in which the first sheet layer 20A and the second sheet layer 20B are bonded only by a melted and solidified material 20*m* corresponding to a most part or a part of at least one of the first sheet layer 20A and the second sheet layer 20B in the sheet bonded portions 40; a second welding mode (see FIG. 17(*b*)) in which the first sheet layer 20A and the second sheet layer 20B are bonded only by a melted and solidified material 30*m* corresponding to a whole, a most part, or a part of the elastic film 30 in the sheet bonded portions 40; and a third welding mode (see FIG. 17(*c*)) obtained by combining these welding modes, and it is preferable to adopt the second and third welding modes. A particularly preferable mode is a mode in which the first sheet layer 20A and the second sheet layer 20B are bonded by the melted and solidified material 20*m* corresponding to a part of the first sheet layer 20A and the second sheet layer 20B and the melted and solidified material 30*m* corresponding to a whole or a most part of the elastic film 30 in the sheet bonded portions 40. The melted and solidified material 30*m* of the elastic film 30 appearing in white is seen in the melted and solidified material 20*m* with the fibers of the first sheet layer 20A or the second sheet layer 20B appearing in black in the third welding mode illustrated in FIG. 19 (*b*), however, the melted and solidified material of the elastic film is not seen in the melted and solidified material 20*m* with the fibers of the first sheet layer 20A or the second sheet layer 20B in the first welding mode illustrated in FIG. 19 (*a*) (a white part corresponds to a boundary of the melted and solidified material 20M with fibers and scattered reflection of the melted and solidified material 20*m* with the fibers and the melted and solidified material 20*m* with the fibers).

In a case in which the first sheet layer 20A and the second sheet layer 20B are bonded using the melted and solidified material 20*m* corresponding to a most part or a part of at least one of the first sheet layer 20A and the second sheet layer 20B as an adhesive as in a first adhesive mode or a third adhesive mode, it is preferable that a part of the first sheet layer 20A and the second sheet layer 20B is not melted in order not to harden the sheet bonded portions 40. When the first sheet layer 20A and the second sheet layer 20B are nonwoven fabric, a case in which a part of the first sheet layer 20A and the second sheet layer 20B is not melted includes a mode in which for all fibers of the sheet bonded portions 40, a core (including a central portion of each component fiber of a conjugate fiber in addition to a core of the conjugate fiber) remains while a surrounding portion (including a portion on a surface layer side of each component fiber of a conjugate fiber in addition to a sheath in the conjugate fiber) melts; a mode in which some fibers do not melt at all while all remaining fibers melt; or a mode in which a core remains while a surrounding portion melts.

Peel strength becomes high when the first sheet layer 20A and the second sheet layer 20B are bonded using the melted and solidified material 30m of the elastic film 30 as an adhesive, as in the second welding mode and the third welding mode. In the second welding mode, under the condition that a melting point of at least one of the first sheet layer 20A and the second sheet layer 20B is higher than a melting point of the elastic film 30 and a heating temperature at the time of forming the sheet bonded portions 40, the elastic film 30 may be interposed between the first sheet layer 20A and the second sheet layer 20B, portions to be the sheet bonded portions 40 may be pressed and heated, and only the elastic film 30 may be melted to perform the welding. Meanwhile, in the third welding mode, under the condition that a melting point of at least one of the first sheet layer 20A and the second sheet layer 20B is higher than the melting point of the elastic film 30, the elastic film 30 may be interposed between the first sheet layer 20A and the second sheet layer 20B, the portions to be the sheet bonded portions 40 may be pressed and heated, and at least one of the first sheet layer 20A and the second sheet layer 20B and the elastic film 30 may be melted to perform the welding. From this point of view, the melting point of the elastic film 30 is preferably about 80 to 145° C., melting points of the first sheet layer 20A and the second sheet layer 20B are preferably about 85 to 190° C., particularly, about 150 to 190° C., and a difference between the melting points of the first sheet layer 20A and the second sheet layer 20B and the melting point of the elastic film 30 is preferably about 60 to 90° C. In addition, the heating temperature is preferably set to about 100 to 150° C.

Figure 18:
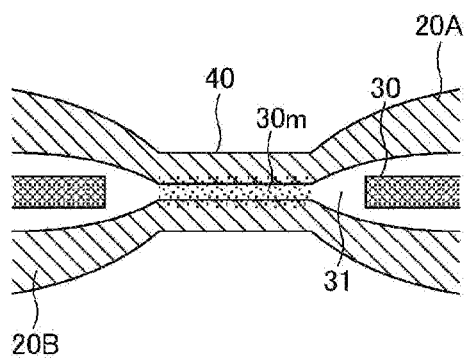
FIGS. 18(a)-18(c) are cross-sectional views schematically illustrating a cross section of the main part of the outer member stretched to a certain extent.
Figure 18:
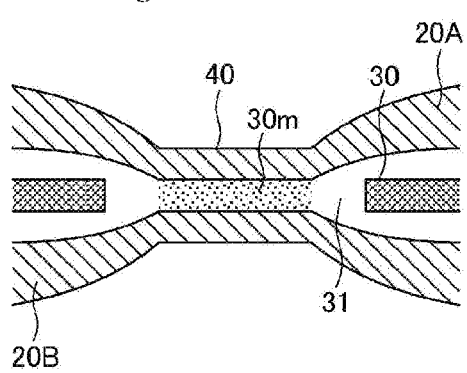
Figure 18:
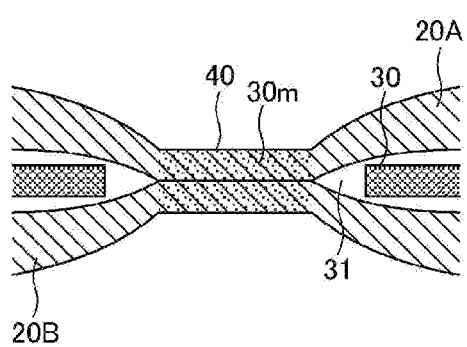

In the second welding mode and the third welding mode, when the first sheet layer 20A and the second sheet layer 20B are nonwoven fabric, the melted and solidified material 30m of the elastic film 30 may infiltrate among fibers across the whole thickness direction of the first sheet layer 20A and the second sheet layer 20B of the sheet bonded portions 40 as illustrated in FIG. 18(c). However, flexibility of the sheet bonded portions 40 becomes high in a mode in which the melted and solidified material 30m infiltrates among fibers in the thickness direction halfway as illustrated in FIGS. 17(b), 17(c), and FIG. 18(a), or a mode in which the melted and solidified material 30m hardly infiltrate among the fibers of the first sheet layer 20A and the second sheet layer 20B as illustrated in FIG. 18(b).

Figure 20:
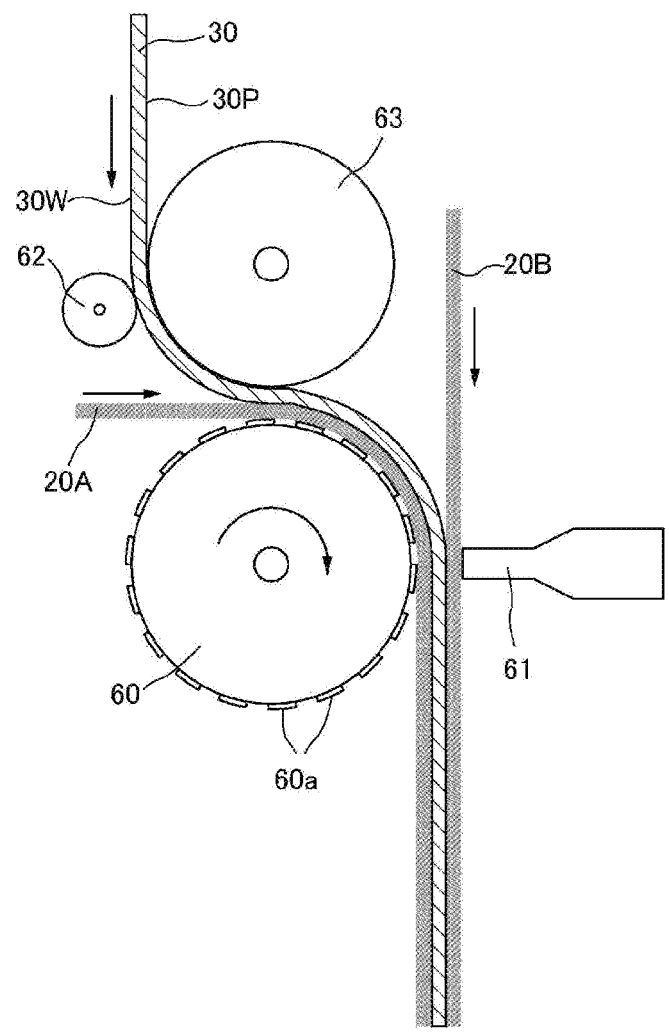
FIG. 20 is a schematic view of an ultrasonic sealing device.

FIG. 20 illustrates an example of an ultrasonic sealing device suitable for forming the second welding mode and the third welding mode. In this ultrasonic sealing device, to form the sheet bonded portions 40, the first sheet layer 20A, the elastic film 30, and the second sheet layer 20B are fed between an ultrasonic horn 61 and an anvil roll 60 having protrusions 60a formed in a pattern of the sheet bonded portions 40 on an external surface. In this instance, for example, when a feed speed of conveyance of the elastic film 30 at an upstream side by a feed drive roll 63 and a nip roll 62 is controlled to be lower than a feed speed of conveyance after the anvil roll 60 and the ultrasonic horn 61, the elastic film 30 is stretched to a predetermined stretch rate in an MD (machine direction, flow direction) on a path from a nip position by the feed drive roll 63 and the nip roll 62 to a sealing position by the anvil roll 60 and the ultrasonic horn 61. A stretch rate of the elastic film 30 may be set by selecting a speed difference between the anvil roll 60 and the feed drive roll 63, and may be set to, for example, about 300% to 500%. Reference symbol 62 denotes the nip roll. The first sheet layer 20A, the elastic film 30, and the second sheet layer 20B fed between the anvil roll 60 and the ultrasonic horn 61 are, in a stacked state in this order, heated by ultrasonic vibration energy of the ultrasonic horn 61 while being pressed between the protrusions 60a and the ultrasonic horn 61. Further, the through holes 31 are formed in the elastic film 30 by melting only the elastic film 30 or melting the elastic film 30 and at least one of the first sheet layer 20A and the second sheet layer 20B. At the same time, the first sheet layer 20A and the second sheet layer 20B are bonded via the through holes 31. Therefore, in this case, an area rate of the sheet bonded portions 40 may be selected by selecting a size, a shape, a separation interval, an arrangement pattern in a roll length direction and a roll circumferential direction, etc. of the protrusions 60a of the anvil roll 60.

Figure 11A:
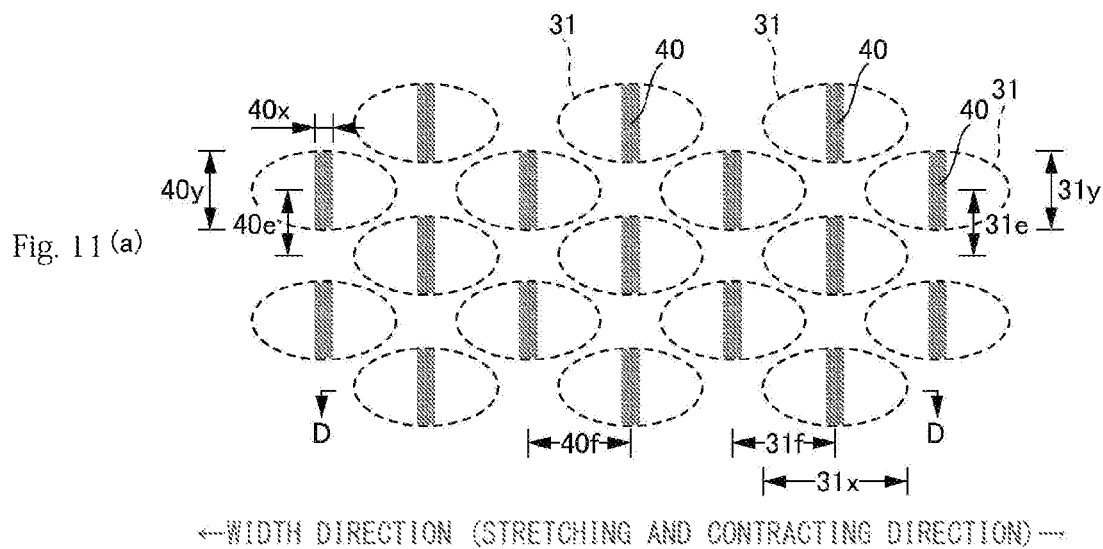
FIG. 11(a) is a plan view of a main part of a non-stretchable region.
Figure 11B:
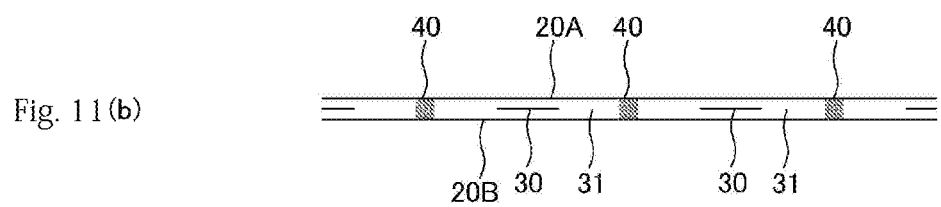
FIG. 11(b) is a D-D cross-sectional view of FIG. 11(a)
Figure 11C:
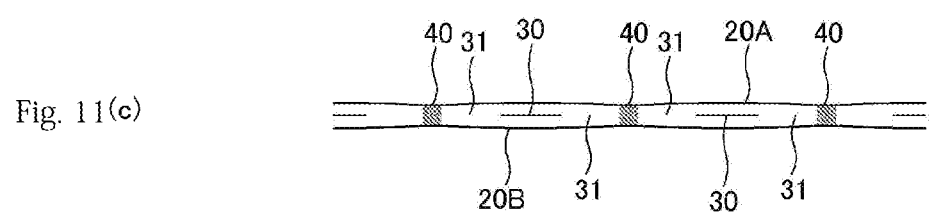
FIG. 11(c) is a cross-sectional view in a worn state.
Figure 11D:
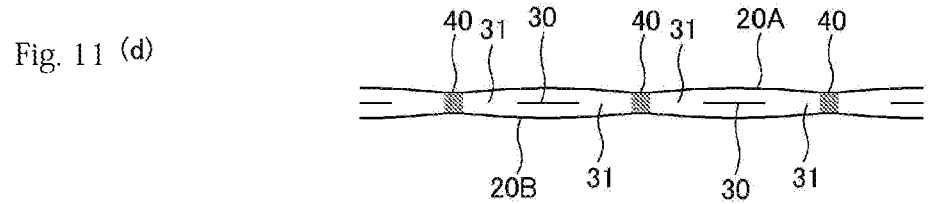
FIG. 11(d) is a cross-sectional view in a natural length state.

Although the reason for formation of the through holes 31 is not necessarily clear, it is considered that openings are formed by melting the elastic film 30 at portions corresponding to the protrusions 60a of the anvil roll 60 so as to be removed from the surroundings. In this instance, a portion between the two adjacent through holes 31 arranged in the stretchable direction in the elastic film 30 is cut at both sides thereof in the stretchable direction by the through holes 31 as illustrated in FIG. 7(a), FIG. 9(a), and FIG. 11(a), and supports at both sides in a contraction direction are lost. Thus, within an extent that continuity in a direction orthogonal to the contraction direction can be maintained, the closer to the central side of the direction orthogonal to the stretchable direction, the more the elastic film 30 contracts to the central side in the stretchable direction to be commensurable so that the through holes 31 are enlarged in the stretchable direction. When the sheet bonded portions 40 are formed in a pattern with sections being left in which the elastic film 30 linearly continues along the stretchable direction, as in a stretchable region 80 described below, and when the elastic film 30 contracts to the natural length state for example by cutting for obtaining individual products, enlarged portions of each through hole 31 contract in the stretchable direction so that gaps cannot be formed between each through hole 31 and each sheet bonded portion 40 as illustrated in FIG. 7(a) and FIG. 9(a). On the other hand, when the sheet bonded portions 40 are formed in a pattern without such sections in which the elastic film 30 linearly continues along the stretchable direction, as in a non-stretchable region 70 described below, even if the elastic film 30 is cut for obtaining the individual products, contraction is not substantially performed, as illustrated in FIG. 11(a). Thus, large gaps are left between each through hole 31 and each sheet bonded portion 40.

Constituent materials of the first sheet layer 20A and the second sheet layer 20B are not particularly limited as long as the materials have sheet shapes and a design printing portion of the elastic film described below can be visually recognized from the outside, and nonwoven fabric is preferably used in view of air permeability and flexibility. The nonwoven fabric may be composed of any raw fiber. Examples of the raw fiber include synthetic fibers, such as olefin fibers, for example, polyethylene fibers and polypropylene fibers, polyester fibers, and polyamide fibers; recycled fibers, such as rayon and cupra; natural fibers, such as cotton; and blend or conjugate fibers composed of two or more of these fibers. The nonwoven fabric may be prepared by any process. Examples of such a process include well-known processes, such as spun lacing, spun bonding, thermal bonding, melt blowing, needle punching, air-through processes, and point bonding. The nonwoven fabric preferably has a basis weight of approximately 12 to approximately 20 g/m². The first sheet layer 20A and the second sheet layer 20B may be composed of a pair of facing layers prepared by folding back a single sheet that is partially or entirely folded back. For example, as in the illustrated mode, in the waist region 23, a component located outer side may be used as the second sheet layer 20B, the folded part 20C formed by folding back to the internal surface side at the waist opening edge thereof may be used as the first sheet layer 20A, and the elastic film 30 may be interposed therebetween, and in the rest part, a component located inner side may be used as the first sheet layer 20A, another component located outer side may be used as the second sheet layer 20B, and the elastic film 30 may be interposed therebetween. The component of the first sheet layer 20A and the component of the second sheet layer 20B may be separately provided across the whole part in the front-back direction, and the elastic film 30 may be interposed between the component of the first sheet layer 20A and the component of the second sheet layer 20B without folding back the component members.

The elastic film 30 may be composed of any thermoplastic resin film having elasticity. For example, it is possible to use a film in which a large number of holes or slits are formed for ventilation in addition to a non-porous film. In particular, it is preferable when the elastic film 30 has a tensile strength in the width direction (the stretchable direction, the MD) of 8 to 25 N/35 mm, tensile strength in the front-back direction (the direction orthogonal to the stretchable direction, the CD) of 5 to 20 N/35 mm, tensile elongation in the width direction of 450 to 1,050%, and tensile elongation in the front-back direction of 450 to 1,400%. The thickness of the elastic film 30 is not particularly restricted. However, the thickness is preferably in a range of about 20 to 40 μm.

(Stretchable Region)

A region having the elastic film stretchable structure 20X in the outer member 20 has a stretchable region which is stretchable in the width direction. The stretchable region 80 has sections 32 in which the elastic film 30 linearly continues along the width direction. The stretchable region contracted in the width direction by a contraction force of the elastic film 30 is extensible in the width direction. More specifically, in a state in which the elastic film 30 is stretched in the width direction, the first sheet layer 20A and the second sheet layer 20B are bonded via the through holes 31 of the elastic film 30 at intervals in the width direction and the front-back direction orthogonal thereto (direction orthogonal to the stretchable direction), and the large number of sheet bonded portions 40 are formed, thereby forming the elastic film stretchable structure 20X. Further, in the stretchable region 80, it is possible to impart elasticity by arranging the through holes 31 such that the stretchable region 80 has the sections in which the elastic film 30 linearly continues along the width direction.

In the stretchable region 80, in the natural length state, as illustrated in FIG. 7 (d) and FIG. 9 (d), the first sheet layer 20A and the second sheet layer 20B between the two adjacent sheet bonded portions 40 are raised in directions away from each other, and thus a contraction wrinkle 25 extending in the front-back direction is formed. Further, as illustrated in FIG. 7 (c) and FIG. 9 (c), even in a worn state stretched to some extent in the width direction, the contraction wrinkles 25 are still remained while being stretched. In addition, as in the illustrated mode, when neither the first sheet layer 20A nor the second sheet layer 20B is bonded to the elastic film 30 except at least between the first sheet layer 20A and the second sheet layer 20B in the sheet bonded portions 40, as is understood from FIG. 7 (c) and FIG. 9 (d) assuming the worn state and FIGS. 7 (a) and 7(b) and FIGS. 9(a) and 9(b) assuming the spread state of the first sheet layer 20A and the second sheet layer 20B, the gaps are formed between each through hole 31 of the elastic film 30 and each sheet bonded portion 40 and in these states, air permeability is imparted by these gaps even when the material of the elastic film 30 is a non-porous film or a non-porous sheet. In addition, in the natural length state illustrated in FIG. 7(d) and FIG. 9(d), the through holes 31 are narrowed due to contraction of the elastic film 30, and the gaps are hardly formed between the through hole 31 and the sheet bonded portion 40. States of the contraction wrinkle 25 in the worn state and the natural length state are shown in also FIG. 8 and FIG. 10.

It is desirable that an elongation at an elastic limit of the stretchable region 80 in the width direction is set to 200% or more (preferably 265% to 295%). The elongation at the elastic limit of the stretchable region 80 is substantially determined by the stretch rate of the elastic film 30 in the manufacturing. However, the elongation at the elastic limit decreases due to a factor that inhibits contraction in the width direction based thereon. A main inhibition factor corresponds to a ratio of the length 40x of the sheet bonded portions 40 to a unit length in the width direction. As this ratio increases, the elongation at the elastic limit decreases. In general, since the length 40x of each of the sheet bonded portions 40 correlates with the area rate of the sheet bonded portions 40, the elongation at the elastic limit of the stretchable region 80 may be adjusted by the area rate of the sheet bonded portions 40.

Stretching stress of the stretchable region 80 may be adjusted mainly by a sum of widths 32w of the sections 32 in which the elastic film 30 linearly continues along the width direction. The width 32w of the section 32 in which the elastic film 30 linearly continues along the width direction is equal to an interval 31d of the through holes 31 in the front-back direction coming into contact with both side edges of the continuing section 32. The interval 31d of the through holes 31 is equal to an interval 40d of the sheet bonded portions 40 in the front-back direction coming into contact with the both side edges of the continuing section in the front-back direction, when the length 31y of the through hole 31 in the front-back direction is equal to the length 40y of the sheet bonded portion 40 in the front-back direction (for example, when a scheme of simultaneously forming the through holes 31 and the sheet bonded portions 40 described above is adopted). Therefore, in this case, the stretching stress of the stretchable region 80 may be adjusted by a ratio of the length 40y of each of the sheet bonded portions 40 to a unit length in the front-back direction. In general, since the length 40y of each of the sheet bonded portions 40 correlates with the area rate of the sheet bonded portions 40, the stretching stress of the stretchable region 80 may be adjusted by the area rate of the sheet bonded portions 40. The stretching stress in stretching to 50% of an elastic limit may be estimated as the stretching stress of the stretchable region 80.

The area rate of the sheet bonded portions 40 and the area of each of the sheet bonded portions 40 in the stretchable region 80 may be appropriately determined. However, in general, the area rate and the areas are preferably set within the following ranges.

Area of each of sheet bonded portions 40: 0.14 to 3.5 mm² (particularly 0.14 to 1.0 mm²)

Area rate of sheet bonded portions 40: 1.8 to 19.1% (particularly 1.8 to 10.6%)

As described above, the elongation at the elastic limit and the stretching stress of the stretchable region 80 may be adjusted by the area of each of the sheet bonded portions 40. Thus, as illustrated in FIG. 15, it is possible to provide a plurality of regions having different area rates of the sheet bonded portions 40 in the stretchable region 80, and to change fitting depending on the sites. In a mode illustrated in FIG. 15, in the front body F, regions 81, each of which is extending in an oblique direction along a groin and edge portion regions 82 of the leg openings, have, when compared to other regions, higher area rates of the sheet bonded portions 40, and thus have smaller stretching stresses, resulting in abilities to stretch flexibly. In addition, in the back body B, ilium facing regions 83 and the edge portion regions 82 of the leg openings have, when compared to other regions, higher area rates of the sheet bonded portions 40, and thus have smaller stretching stresses, resulting in abilities to stretch flexibly.

(Non-Stretchable Region)

In a region having the elastic film stretchable structure 20X in the outer member 20, as illustrated in FIG. 15, it is possible to provide the non-stretchable region 70 on at least one side of the stretchable region 80 in the width direction. Arrangement of the stretchable region 80 and the non-stretchable region 70 may be appropriately determined. In the case of the outer member 20 of the underpants-type disposable diaper in the present embodiment, a portion overlapping with the absorber 13 is a region unnecessary to stretch and contract. Thus, as in the illustrated mode, apart or a whole of the portion overlapping with the absorber 13 (it is desirable to include substantially the entire internal and external fixed region 10B) is preferably set to the non-stretchable region 70. It is as a matter of course possible to provide the non-stretchable region 70 with a range beyond the region overlapping with the absorber 13 to a region not overlapping with the absorber 13 located adjacent to the non-stretchable region 70 in the width direction or the front-back direction thereof, or it is possible to provide the non-stretchable region 70 only in the region not overlapping with the absorber 13.

The non-stretchable region 70 is configured, even though the elastic film 30 continues in the width direction, so as not to have a section in which the elastic film 30 linearly continues along the width direction, due to the presence of the through holes 31. Therefore, even though the elastic film stretchable structure 20X is configured as a whole to include both the stretchable region 80 and the non-stretchable region 70 by bonding the first sheet layer 20A and the second sheet layer 20B via the through holes 31 of the elastic film 30 to form the large number of sheet bonded portions 40 at intervals in the width direction and the front-back direction orthogonal thereto while the elastic film 30 is stretched in the width direction, in the non-stretchable region 70, the elastic film 30 does not linearly continue along the width direction as illustrated in FIG. 11. Thus, the contraction force of the elastic film 30 hardly acts on the first sheet layer 20A and the second sheet layer 20B, elasticity is almost lost, and the elongation at the elastic limit approaches 100%. Further, in the non-stretchable region 70, the first sheet layer 20A and the second sheet layer 20B are bonded by the large number of sheet bonded portions 40 arranged at intervals, and the sheet bonded portions 40 are discontinuous. Thus, a decrease in flexibility is prevented. In other words, it is possible to form the stretchable region 80 and the non-stretchable region 70 depending on the presence or absence of the section in which the elastic film 30 does not linearly continue along the width direction. In addition, continuity of the elastic film 30 still remains in the non-stretchable region 70. As understood from FIG. 12, since an independent cut piece of the elastic film 30 is not left, and no wrinkle is formed, appearance is extremely excellent, and air permeability in the thickness direction by the through holes 31 is ensured. In the non-stretchable region 70, the elongation at the elastic limit in the width direction is preferably 120% or less (preferably 110% or less, more preferably 100%).

An arrangement pattern of the through holes 31 in the elastic film 30 in the non-stretchable region 70 may be appropriately determined. However, when staggered arrangement is adopted as illustrated in FIG. 11, and a pattern in which a center-to-center interval 31$e$ of the through holes 31 in the front-back direction is shorter than the length 31$y$ of each of the through holes 31 in the front-back direction is adopted, linear continuity in the width direction may be almost completely eliminated while maintaining continuity of the elastic film 30, and appearance is preferable as illustrated in FIG. 12. In this case, it is more preferable that a center-to-center interval 31$f$ of the through holes 31 in the width direction is shorter than a length 31$x$ of each of the through holes 31 in the width direction.

In general, especially when stretching stress is in a range of 4 to 12 N/35 mm in stretching the elastic film 30 four times in the width direction, in a state in which the non-stretchable region 70 is stretched to the elastic limit in the width direction, the center-to-center interval 31$e$ of the through holes 31 in the front-back direction is preferably in a range of 0.4 to 2.7 mm, and the length 31$y$ of each of the through holes 31 in the front-back direction is preferably in a range of 0.5 to 3.0 mm, particularly in a range of 0.7 to 1.1 mm. In addition, the center-to-center interval 31$f$ of the through holes 31 in the width direction is preferably 0.5 to 2 times, particularly 1 to 1.2 times the length 31$y$ of the through holes 31 in the front-back direction, and the length 31$x$ of each of the through holes 31 in the width direction is preferably 1.1 to 1.8 times, particularly 1.1 to 1.4 times the center-to-center interval 31$f$ of the through holes 31 in the width direction. In a state in which the non-stretchable region 70 is stretched to an elastic limit in the width direction (in other words, in a state in which the first sheet layer 20A and the second sheet layer 20B are completely spread), the center-to-center interval 31$f$ of the through holes 31 in the width direction is equal to a center-to-center interval 40$f$ of the sheet bonded portions 40 in the width direction, the center-to-center interval 31$e$ of the through holes 31 in the front-back direction is equal to a center-to-center interval 40$e$ of the sheet bonded portions 40 in the front-back direction, and the length 31$y$ of each of the through holes 31 in the front-back direction is equal to the length 40$y$ of each of the sheet bonded portions 40 in the front-back direction.

In a case in which neither the first sheet layer 20A nor the second sheet layer 20B is bonded to the elastic film 30 except between the first sheet layer 20A and the second sheet layer 20B in the sheet bonded portions 40 in the non-stretchable region 70, and the gaps, which are generated by the peripheral edge of each of the through holes 31 of the elastic film 30 and each of the sheet bonded portions 40 separated from each other, are included at both sides of each of the sheet bonded portions 40 in the width direction in the natural length state, air permeability is imparted at all times due to the gaps even if the material of the elastic film 30 is a non-porous film or a non-porous sheet, and thus such a case is preferable. In the case of adopting a scheme of simultaneously forming the through holes 31 and the sheet bonded portions 40 described above, this state is automatically obtained irrespective of a shape of the sheet bonded portions 40, etc.

The shape of each of the sheet bonded portions 40 and the through holes 31 in the natural length state is not particularly restricted. However, it is desirable to have a small area from a viewpoint of flexibility, and it is desirable to have a shape which is long in the front-back direction to eliminate linear continuity in the width direction of the elastic film 30. Thus, it is preferable to adopt an ellipse which is long in the front-back direction, a rectangle (see FIG. 11 and FIG. 13(d)), the rhombus (see FIG. 13(b)), the convex lens shape (see FIG. 13(a)), and the concave lens shape (see FIG. 13 (c)). However, when corners are acute as in the rhombus, the elastic film 30 is easily fractured. In contrast, the convex lens shape is preferable since welding of the sheet bonded portions 40 is stabilized, and the concave lens shape is preferable in that an area may be further reduced.

It is possible to appropriately determine the area rate of the sheet bonded portions 40 and the area of each of the sheet bonded portions 40 in the non-stretchable region. However, in general, ranges below are preferable since the area of each of the sheet bonded portions 40 is small, the area rate of the sheet bonded portions 40 is low, and thus the non-stretchable region 70 is not hardened.

Area of each of sheet bonded portions 40: 0.10 to 0.75 mm$^2$ (particularly 0.10 to 0.35 mm$^2$)

Area rate of sheet bonded portions 40: 4 to 13% (particularly 5 to 10%)

As described above, the elongation at the elastic limit of the non-stretchable region 70 may be changed by the arrangement pattern of the through holes 31, dimensions of each of the through holes 31, and the center-to-center interval of the through holes 31. Therefore, although not illustrated, it is possible to make the elongation at the elastic limit different between a plurality of positions in the stretchable region 80 or a plurality of non-stretchable regions 70. For example, in a preferable mode, the elongation at the elastic limit in the non-stretchable region 70 of the front body F is set to be larger than the elongation at the elastic limit in the non-stretchable region 70 of the back body B.

Even though the non-stretchable region 70 has a section that linearly continues along the width direction similarly to the stretchable region, since the area rate of the sheet bonded portions in the non-stretchable region 70 is higher than that in the stretchable region, the elongation at the elastic limit is remarkable in the non-stretchable region 70. Specifically, it is possible to adopt another mode for eliminating elasticity such as a mode in which the elongation at the elastic limit is 130% or less, a mode in which cutting is performed in the width direction at one position or a plurality of positions as in a conventional stretchable structure using a rubber thread, etc.

(Design Printing Portion)

Figure 14:
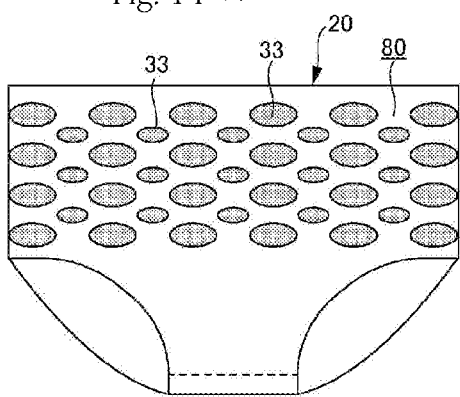
FIGS. 14(a) and 14(b) are explanatory diagrams illustrating a change due to stretching and contraction of an elastic film.
Figure 14:
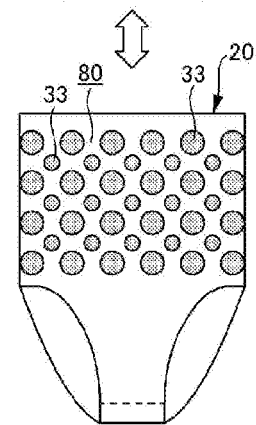
Figure 14:
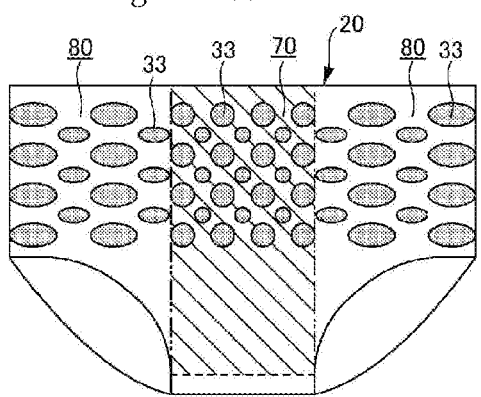
Figure 14:
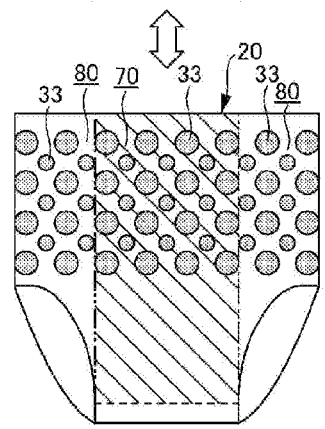

Characteristically, as illustrated in FIG. 2, FIG. 14, and FIG. 15, a design printing portion 33 is provided in a portion located in the stretchable region 80 of the elastic film 30. Since no wrinkles and pleats are formed on the elastic film 30, even though it is stretched and contracted, the damage of the design, which would be caused by formation of wrinkles and pleats on a design printing object, does not occur. In addition to the advantage of not affecting the elasticity of the stretchable region 80 at all, there are advantages that the surface of the elastic film 30 is excellent in printability when compared to the nonwoven fabric, and printing is less likely to peel off since a printed surface of the elastic film 30 is covered with the first sheet layer 20A and the second sheet layer 20B.

To provide the design printing portion 33 in the elastic film 30, the elastic film 30 on which the design printing portion 33 is printed in advance may be used in a portion to be the stretchable region 80 at the time of manufacture, or the design printing portion 33 may be printed on the portion to be the stretchable region 80 in the elastic film 30 in manufacturing line prior to stretching of the elastic film 30 (at an upstream side of the feed drive roll 63 and the nip roll 62 in the manufacturing method of FIG. 20). The printing method is not particularly limited, and may correspond to typography, gravure printing, offset printing, inkjet printing, etc. In order to improve the printability of the elastic film 30, it is desirable to perform corona treatment on the printed surface.

Design of the design printing portion 30 is not particularly limited. Examples thereof may include a pattern for decoration (including an illustration and a one-point character in addition to a Polka dot pattern and a flower pattern), a function indication such as a usage method, usage guide, or a size, etc., or a mark indication such as a manufacturer, a product name, or a distinctive function, or a combination thereof.

The design printing portion 33 may be provided in a part of the elastic film 30 or across the entire elastic film 30. In the illustrated mode, it is presumed that each design printing portion 33 having a uniform pattern is provided, and the design printing portion 33 is provided across the entire part in the width direction in a part in the front-back direction. However, it is possible to provide the design printing portion 33 only in the intermediate portion L in the width direction or on both sides in the width direction in a part or the entire part in the front-back direction. In addition, as illustrated in FIG. 14(b), the design printing portion 33 may be provided in a part or the entire part of the non-stretchable region 70 in addition to the stretchable region 80.

When the design printing portion 33 is provided on the elastic film 30, the design printing portion 33 is deformed as the elastic film 30 stretches and contracts. In this case, as illustrated in FIG. 14(a), when the entire design printing portion 33 uniformly stretches and contracts, a shape of the design printing portion 33 is uniformly deformed, and thus an overall balance of the design printing portion 33 can be maintained. However, the elastic film stretchable structure 20X is provided with a plurality of stretchable regions 80 having different elongations at the elastic limit by making patterns of the sheet bonded portions 40 different for obtaining an advantage that fitting, stretchable/non-stretchable and the like may be changed depending on the sites. Such plurality of regions having different elongations at the elastic limit is formed by a difference in the amount of the extent of contracting of the elastic film 30 after tension, which has been applied to the first sheet layer 20A, the second sheet layer 20B, and the elastic film 30 therebetween, is released by cutting into individual products or parts after the sheet bonded portions 40 are formed in a manufacturing process. The extent of contracting (including a case of non-stretchable state in which contraction hardly occurs) of the elastic film 30 is decreased to be lower than a stretch rate of the elastic film 30, which has been stretched the sheet bonded portions 40 are formed, and the degree of such decrease may be changed depending on the patterns of the sheet bonded portions 40. When the design printing portion 33 is uniformly provided so as to be disposed in portions to be the plurality of regions in the elastic film 30, a deformation degree in the stretchable direction of the design printing portion 33 differs for each region in the natural length state or the worn state, and the appearance deteriorates.

Figure 22A:
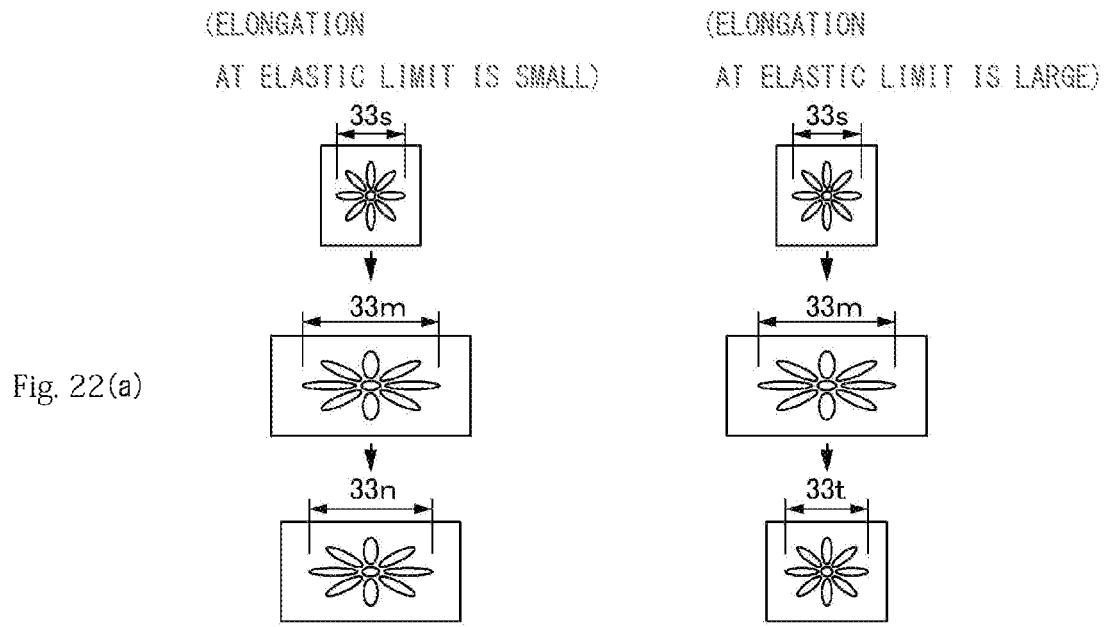
FIGS. 22(a) and 22(b) are explanatory diagrams illustrating a relationship between a print pattern and a finish.
Figure 22:
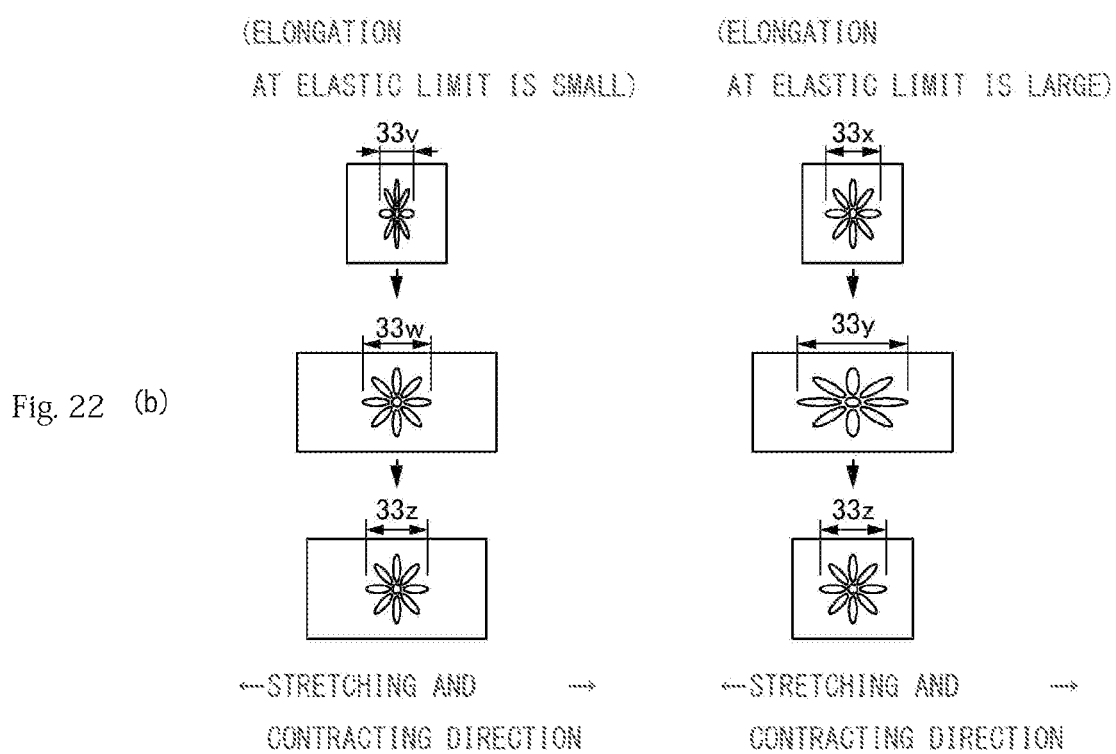

For example, a case in which the design printing portion is applied in a manufacturing process is discussed. There are a region in which the elongation at the elastic limit is small and a region in which the elongation at the elastic limit is large, as illustrated in FIG. 22(a), and a standard dimension 33s of the design printing portion 33 in the stretchable direction is set to 100 before the elastic film 30 is stretched, and the stretch rate of the elastic film 30 at the time of forming the sheet bonded portions 40 is set to 200%. A dimension 33m of the design printing portion 33 in the stretchable direction at the time of forming the sheet bonded portions 40 is 200. Thus, in the natural length state, the extent of contracting is small in a region in which the elongation at the elastic limit is small. For example, when the extent of contracting thereof is set to 20, a dimension 33n of the design printing portion 33 in the stretchable direction is 180. On the other hand, the extent of contracting is large in a region in which the elongation at the elastic limit is large. For example, when the extent of contracting thereof is set to 80, a dimension 33t of the design printing portion 33 in the stretchable direction is 120. A deformation difference in the stretchable direction of the design printing portion 33 between the both regions is largely different.

On the other hand, the region has the smaller elongation at the elastic limit, that is, the region has the smaller extent of contracting after the sheet bonded portions 40 are formed by stretching the elastic film 30, at the higher rate, a deformed design contracted and deformed in the stretchable direction is printed. By doing so, a difference in deformation rate in the stretching and contracting direction of the design printing portion 33 becomes small between the regions, and deterioration of appearance may be prevented. Here, the deformation rate means a percentage of a difference in length before and after contraction and deformation to a length before contraction and deformation. For example, considering in the same condition as that of a specific example illustrated in FIG. 22(a), when a deformed design which is contracted and deformed at a high deformation rate, for example, 50% in the stretchable direction and has a dimension in the stretchable direction set to 33v is printed in advance as illustrated in FIG. 22(b), a dimension 33w of the design printing portion 33 in the stretchable direction is stretched to 200% and becomes 100 at the time of forming the sheet bonded portions 40, and a dimension 33z of the design printing portion 33 in the stretchable direction in the natural length state is recovered by 20 and becomes 80. In addition, in a region in which the elongation at the elastic limit is large, contraction and deformation occur in advance at a low deformation rate, for example, 20%. When a deformed design having a dimension of 80 in which a dimension in the stretchable direction is set to 33x is printed, a dimension 33y of the design printing portion 33 in the stretchable direction is stretched to 200% and becomes 160 at the time of forming the sheet bonded portions 40, and a dimension 33z of the design printing portion 33 in the stretchable direction in the natural length state recovers by 80 and becomes 80. That is, a deformation difference in the stretchable direction of the design printing portion 33 between the both regions may be decreased.

A deformation rate of the deformed design may be appropriately determined. However, for example, as illustrated in FIG. 14 (b), in a case in which the design printing portion is provided in the stretchable region and the non-stretchable region, in order to make appearance close to a standard magnification (100%) in the natural length state, and to reduce a difference in formation between the both regions, it is preferable that the deformation rate of the deformed design printed in the stretchable region is set to about 20 to 40%, and the deformation rate of the deformed design printed in the non-stretchable region is set to about 60 to 80%. In addition, in order to make appearance close to the standard magnification (100%) in the stretched state at the time of wearing, and to reduce a difference in formation between the both regions, it is preferable that the deformation rate of the deformed design printed in the stretchable region is set to about 45 to 55%, and the deformation rate of the deformed design printed in the non-stretchable region is set to about 60 to 80%.

In addition, in a case in which a plurality of regions having the different elongations at the elastic limit is provided, when the design printing portion 33 straddling a boundary of the regions is included, there is concern that deformation may be nonuniform at both sides of the boundary, and appearance may deteriorate. Therefore, in the case in which the plurality of regions having different elongations at the elastic limit is provided, it is a preferable mode that the design printing portion 33 is not disposed at the boundary of the plurality of regions or at portions adjacent to the boundary on both sides of the boundary. It is preferable that a total width of the portions adjacent to the boundary of the plurality of regions is set to about 3 to 10 mm.

For example, when welding of the sheet bonded portions 40 is performed by ultrasonic sealing, the recesses of unevenness, which are formed on the sheet layer on the anvil roll 60 side become deeper, whereas the recesses, which are formed on the opposite sheet layer, becomes shallower. This description is applied to the heat sealing. In the elastic film stretchable structure 20X, the design printing portion 33 on the elastic film 30 is visually recognized through the first sheet layer 20A or the second sheet layer 20B. Therefore, in a case in which the design printing portion 33 is provided on the elastic film 30, when the design printing portion 33 is provided on a surface of the elastic film on a side of a sheet layer (shallower-uneven-layer) having shallower recesses and shallower unevenness, there is an advantage that appearance of the design printing portion 33 is improved. Such a structure may be manufactured by supplying the elastic film 30 such that the design printing portion 33 is included in a surface 30P of the elastic film 30 on the side being opposite to the anvil roll 60 side in the elastic film 30 at the time of forming the sheet bonded portions 40. In particular, according to the present manufacturing method, as for the pleats formed on the first sheet layer 20A and the second sheet layer 20B of the stretchable region 80 in the natural length state, the pleats of the sheet layer on the side being opposite (20B in the illustrated mode) to the anvil roll 60 side are more neatly formed in order than those on the sheet layer on the anvil roll side, so that the appearance of the design printing portion 33 is further improved in this respect.

In the elastic film stretchable structure 20X, since the design printing portion 33 on the elastic film 30 is visually recognized through the first sheet layer 20A or the second sheet layer 20B, a light transmittance of a layer on a visually viewed side corresponding to one of the first sheet layer 20A or the second sheet layer 20B is preferably high, for example, 60% or more, particularly 80% or more. The light transmittance is measured, for example, using a flicker photometric color difference meter Z-300A manufactured by Nippon Denshoku Industries Co., Ltd. as follows. That is, first, measurement is performed in a state in which a shielding material for shielding light is disposed between one detecting unit and another detecting unit, and the zero point is corrected. Subsequently, after the shielding material disposed between the one detecting unit and the other detecting unit is removed, measurement is performed in a state in which there is no light shielding, and standard correction is performed. Subsequently, an outer sheet as an object is measured while being disposed between the one detecting unit and the other detecting unit.

Figure 23:
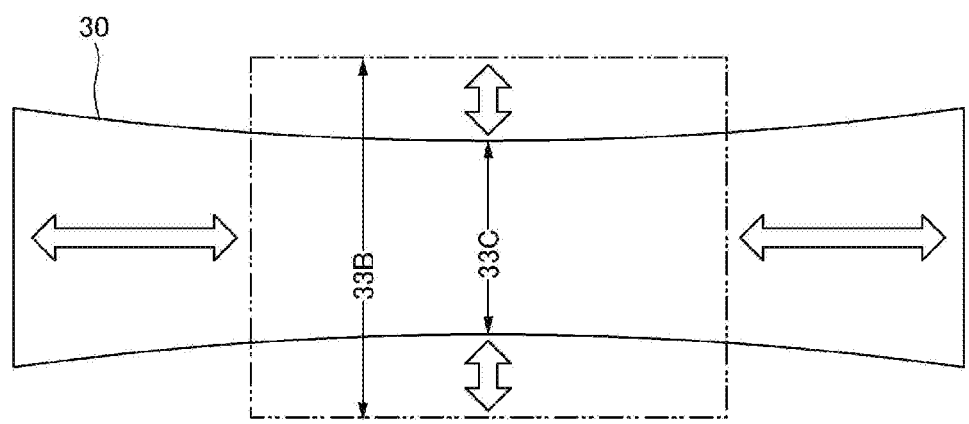
FIG. 23 is an explanatory diagram of WIDTH-DECREASING of the elastic film.

As described above, the elastic film 30 is not particularly limited. However, since the design printing portion 33 is provided, WIDTH-DECREASING in the direction orthogonal to the stretchable direction becomes a problem. In more detail, as illustrated in FIG. 23, when the elastic film 30 is changed from a natural length state indicated by a two-dot chain line to a state elongated to one direction indicated by a solid line, a width in a direction orthogonal to a stretching direction narrows toward a center in the stretchable direction depending on the amount of stretching, which is referred to as the WIDTH-DECREASING (or Neck-in). A "WIDTH-DECREASING rate" indicating a degree thereof refers to "(33B−33C)/33B×100", when a minimum width (a width in a middle in a length direction), in stretching the elastic film 30 having a width 33B until 3.5 times in the length direction, is set to 33C. When the elastic film 30 is contracted from this WIDTH-DECREASING state to the natural length, the width returns to the original width. In many cases, the amount of stretching in the stretchable direction changes depending on the position in the direction orthogonal to the stretchable direction so that the stretchable region 80 fits a body having complicated curved surfaces. In such a case, a degree of the WIDTH-DECREASING changes depending on the position in the direction orthogonal to the stretchable direction. Therefore, when the amount of stretching in the stretchable direction changes depending on the position in the direction orthogonal to the stretchable direction in providing the design printing portion 33 on the elastic film 30 in the portion located in the stretchable region 80, the amount of deformation of the design printing portion 33 due to the WIDTH-DECREASING of the elastic film 30 changes depending on the position in the direction orthogonal to the stretchable direction, and there is concern that appearance may deteriorate. Therefore, it is desirable that the elastic film 30 has a small WIDTH-DECREASING rate, particularly 25% or less, more preferably 20% or less. When such an elastic film 30 having a small WIDTH-DECREASING rate is used, production stability and printability in manufacturing line become excellent.

<Description of terms in specification>

The terms used in the specification have the following meanings unless otherwise stated.

The "front body" and the "back body" refer to front and back portions using the center of the underpants-type disposable diaper in the front-back direction as a boundary. In addition, the crotch portion refers to a front-back direction range including the center of the underpants-type disposable diaper in the front-back direction, and refers to a front-back direction range of a portion having a narrower part when the absorber has the narrower part.

The "elongation at the elastic limit" refers to an elongation at an elastic limit in the stretchable direction (in other words, a state in which the first sheet layer and the second sheet layer are completely spread), and expresses a length at the time of the elastic limit as a percentage when the natural length is set to 100%.

The "area rate" refers to a rate of a target portion to a unit area, and expresses the rate as a percentage by dividing a total area of the target portions (for example, the sheet bonded portions 40, the openings of the through holes 31, and the vent hole) in a target region (for example, the stretchable region 80, the non-stretchable region 70, a main stretchable portion, and a damping elastic portion) by an area of the target region. Particularly, an "area rate" in a region having a stretchable structure refers to an area rate in a state of being stretched in the stretchable direction to the elastic limit. In a mode in which a large number of target portions are provided at intervals, it is desirable to obtain the area rate by using the target region of a size including ten or more target portions.

The "stretch rate" represents a value relative to the natural length (100%)

The "basis weight" is determined as follows: After the sample or test piece is preliminarily dried, it is allowed to stand in a test room or apparatus under normal conditions (the test location is at a temperature: 20±5° C., relative humidity: 65% or less) until the constant mass. The preliminary drying is to make the sample or test piece be constant mass in an environment within a relative humidity of 10 to 25% and at a temperature not exceeding 50° C. The fibers of an official moisture regain of 0.0% does not need preliminary drying. A cut sample with a size of 200 mm by 250 mm (±2 mm) is cut from the test piece in the constant mass, with a cutting template (200 mm by 250 mm, ±2 mm). The sample is weighed and the weight is multiplied by 20 into the weight per square meter. The resulting value is defined as the basis weight.

The "thickness" of the absorber is measured using a thickness measurement apparatus of OZAKI MGF Co., Ltd. (PEACOCK, Dial Thickness Gauge Large Type, Model J-B (Measurement Range 0 to 35 mm) or Model K-4 (Measurement Range 0 to 50 mm)) by horizontally disposing a sample and the thickness measurement apparatus.

A "thickness" other than the above-described thickness is automatically determined with an automatic thickness gauge (KES-G5 handy compression measurement program) under the conditions of a load of 10 gf/cm$^2$ and a pressurization area of 2 cm$^2$.

The "tensile strength" and the "tensile elongation (elongation at break)" are measured at an initial chuck interval of 50 mm and a speed of testing of 300 mm/min with a tensile tester (for example, AUTOGRAPH AGS-G100N available from SHIMADZU) in accordance with JIS K7127:1999 "Plastics—Determination of tensile properties", except that the test piece is a rectangle with a width of 35 mm and a length of 80 mm.

The "stretching stress" indicates the tensile stress (N/35 mm) when the sample is stretched in an elastic region that is measured by a tensile test at an initial chuck interval (distance between marked lines) of 50 mm and a speed of testing of 300 mm/min in accordance with JIS K7127:1999 "Plastic—Determination of tensile properties", and an extent of stretching may be appropriately determined depending on the test object. A test piece is preferably formed in a rectangular shape having a width of 35 mm and a length of 80 mm or more. If a test piece with a width of 35 mm cannot be prepared, the test piece with a maximum possible width is prepared and the observed value is converted into a value at a width of 35 mm. Even if a sufficiently large test piece cannot be prepared from a target region with a small area, small test pieces can also be used for comparison of the stretching stress. For example, AUTOGRAPHAGS-G100N manufactured by SHIMADZU may be used as a tensile tester.

The "spread state" refers to a flatly spread state without contraction or slack.

Unless otherwise specified, dimensions of each portion refer to dimensions in the spread state, not the natural length state.

In the absence of description about an environmental condition in a test or measurement, the test or measurement is performed in a test room or apparatus under normal conditions (the test location is at a temperature 20±5° C., relative humidity 65% or less).

INDUSTRIAL APPLICABILITY

The invention may be generally used for an absorbent article having a stretchable region such as a sanitary napkin, various disposable diapers such as a tape-type disposable diaper, an underpants-type disposable diaper, etc. in addition to the underpants-type disposable diaper in the above example, etc.

REFERENCE SIGNS LIST

B . . . back body, F . . . front body, T . . . lower torso portion, L . . . intermediate portion, 10 . . . inner member, 10B . . . internal and external fixed region, 11 . . . liquid pervious top sheet, 12 . . . liquid impervious sheet, 13 . . . absorber, 13N . . . narrower part, 14 . . . wrapping sheet, 95 . . . gather nonwoven fabric, 96 . . . gather elastic member, 17 . . . non-absorber side portion, 20 . . . outer member, 20A . . . first sheet layer, 20B . . . second sheet layer, 20C . . . folded part, 20X . . . elastic film stretchable structure, 21 . . . side seal portion, 23 . . . waist region, 24 . . . waist portion elastic member, 25 . . . contraction wrinkle, 29 . . . leg line, 30 . . . elastic film, 31 . . . through hole, 40 . . . sheet bonded portion, 70 . . . non-stretchable region, 80 . . . stretchable region, 84 . . . weak stretchable region, 90 . . . three-dimensional gather, 33 . . . design printing portion.

The invention claimed is:

1. An absorbent article having an elastic film stretchable structure in which an elastic film is stacked between a first sheet layer and a second sheet layer, and the first sheet layer and the second sheet layer are bonded together directly or through the elastic film by a large number of sheet bonded portions arranged at intervals, wherein:
a region having the elastic film stretchable structure includes a stretchable region,
the stretchable region contracted in a stretchable direction by a contraction force of theelastic film is extensible in the stretchable direction,
a design printing portion is provided in the stretchable region,
the design printing portion is printed on the elastic film so as to have a shape to be deformed as the elastic film stretches and contracts,
at each of the sheet bonded portions, the first sheet layer and the second sheet layer are welded via a through-hole penetrating the elastic film and first recesses having a first depth are formed in a surface of the first sheet layer that is not facing the second sheet layer and second recesses having a second depth are formed in a surface of the second sheet layer that is not facing the first sheet layer,
the second depth is shallower than the first depth, and
the design printing portion is provided on a surface of the elastic film facing the second sheet layer.

2. The absorbent article according to claim 1, wherein the stretchable region is stretchable in only one direction, and the elastic film has a width-decreasing rate of 25% or less in a direction orthogonal to the stretchable direction.

3. The absorbent article according to claim 2, wherein the elastic film stretchable structure includes a plurality of regions having different elongations at an elastic limit, and the design printing portion is not disposed at a boundary of the plurality of regions or at portions adjacent to the boundary on the both sides thereof in the elastic film.

4. The absorbent article according to claim 2, wherein the absorbent article is an underpants-type disposable diaper including:
an outer member disposed in a front body and a back body,
an inner member fixed to the outer member, the inner member including an absorber,
side seal portions at which both side portions of the outer member in the front body and both side portions of the outer member in the back body are bonded together, respectively,
an annular lower torso portion,
a waist opening, and
a pair of left and right leg openings,
wherein the outer member in at least one of the front body and the back body has the elastic film stretchable structure such that the stretchable direction of the stretchable region is a width direction, across a range corresponding to a space between the side seal portions totally in the width direction and at least partly in a front-back direction.

5. The absorbent article according to claim 1, wherein the elastic film stretchable structure includes a plurality of regions having different elongations at an elastic limit, and the design printing portion is not disposed at a boundary of theplurality of regions or at portions adjacent to the boundary on the both sides thereof in the elastic film.

6. The absorbent article according to claim 5, wherein the absorbent article is an underpants-type disposable diaper including:
an outer member disposed in a front body and a back body,
an inner member fixed to the outer member, the inner member including an absorber,
side seal portions at which both side portions of the outer member in the front body and both side portions of the outer member in the back body are bonded together, respectively,
an annular lower torso portion,
a waist opening, and
a pair of left and right leg openings,
wherein the outer member in at least one of the front body and the back body has the elastic film stretchable structure such that the stretchable direction of the stretchable region is a width direction, across a range corresponding to a space between the side seal portions totally in the width direction and at least partly in a front-back direction.

7. The absorbent article according to claim 1, wherein the absorbent article is an underpants-type disposable diaper including:
   an outer member disposed in a front body and a back body,
   an inner member fixed to the outer member, the inner member including an absorber,
   side seal portions at which both side portions of the outer member in the front body and both side portions of the outer member in the back body are bonded together, respectively,
   an annular lower torso portion,
   a waist opening, and
   a pair of left and right leg openings,
   wherein the outer member in at least one of the front body and the back body has the elastic film stretchable structure such that the stretchable direction of the stretchable region is a width direction, across a range corresponding to a space between the side seal portions totally in the width direction and at least partly in a front-back direction.

8. A method of manufacturing an absorbent article having an elastic film stretchable structure that includes a stretchable region stretchable in one direction, the method comprising:
   in forming the elastic film stretchable structure, forming sheet bonded portions by bonding a first sheet layer and a second sheet layer directly by ultrasonic sealing, which is performed with the first sheet layer, the elastic film, and the second sheet layer passed between an anvil roll and an ultrasonic horn in a state in which the elastic film is interposed between the first sheet layer and the second sheet layer while being stretched in a stretchable direction of the stretchable region at a large number of positions arranged at intervals; and
   as the elastic film, using an elastic film on which a design printing portion is printed in advance in a portion to be the stretchable region, or
   printing the design printing portion in the portion to be the stretchable region in the elastic film in manufacturing line, prior to stretching of the elastic film; and
   supplying the elastic film such that the design printing portion is disposed in a surface of the elastic film, the surface being on a side opposite to the anvil roll side;
   wherein the design printing portion has a shape to be deformed as the elastic film stretches and contracts.

9. The method of manufacturing an absorbent article according to claim 8, wherein the elastic film has a width-decreasing rate of 25% or less in a direction orthogonal to the stretchable direction.

10. The method of manufacturing an absorbent article according to claim 9, further comprising:
    in forming the elastic film stretchable structure, forming a plurality of stretchable regions having different elongations at an elastic limit by making patterns of the sheet bonded portions different; and
    printing the design printing portion in portions to be the plurality of stretchable regions in the elastic film;
    wherein in the printing, a region has the smaller elongation at the elastic limit, at the higher deformation rate, a deformed design contracted and deformed in the stretchable direction is printed.

11. The method of manufacturing an absorbent article according to claim 8, further comprising:
    in forming the elastic film stretchable structure, forming a plurality of stretchable regions having different elongations at an elastic limit by making patterns of the sheet bonded portions different; and
    printing the design printing portion in portions to be the plurality of stretchable regions in the elastic film;
    wherein in the printing, a region has the smaller elongation at the elastic limit, at the higher deformation rate, a deformed design contracted and deformed in the stretchable direction is printed.

12. The method of manufacturing an absorbent article according to claim 8, further comprising:
    in forming the elastic film stretchable structure, a plurality of regions, which have different elongations at the elastic limit in a product state is formed;
    wherein the design printing portion is not printed at a boundary of the plurality of regions or at portions adjacent to the boundary on the both sides thereof in the elastic film.

* * * * *

UNITED STATES PATENT AND TRADEMARK OFFICE
CERTIFICATE OF CORRECTION

| | |
|---|---|
| PATENT NO. | : 11,266,550 B2 |
| APPLICATION NO. | : 16/078362 |
| DATED | : March 8, 2022 |
| INVENTOR(S) | : Takaishi |

It is certified that error appears in the above-identified patent and that said Letters Patent is hereby corrected as shown below:

In the Claims

Column 25, Line 66 of Claim 1:
"theelastic film…"
Should instead read:
--the elastic film….--

Column 26, Line 50 of Claim 5:
"…theplurality of regions…"
Should instead read:
--… the plurality of regions…--

Signed and Sealed this
Tenth Day of May, 2022

Katherine Kelly Vidal
*Director of the United States Patent and Trademark Office*